(12) United States Patent
Jimenez et al.

(10) Patent No.: US 8,945,208 B2
(45) Date of Patent: Feb. 3, 2015

(54) METHODS OF VALVE DELIVERY ON A BEATING HEART

(71) Applicant: Edwards Lifesciences Corporation, Irvine, CA (US)

(72) Inventors: Teodoro S. Jimenez, Irvine, CA (US); Walter Lee, Irvine, CA (US); Mark Dehdashtian, Irvine, CA (US); Kristopher J. Yee, Huntington Beach, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 13/922,129

(22) Filed: Jun. 19, 2013

(65) Prior Publication Data

US 2013/0345798 A1 Dec. 26, 2013

Related U.S. Application Data

(63) Continuation of application No. 12/835,546, filed on Jul. 13, 2010, now Pat. No. 8,475,522.

(60) Provisional application No. 61/225,510, filed on Jul. 14, 2009.

(51) Int. Cl.
*A61F 2/24* (2006.01)
*A61M 25/01* (2006.01)

(52) U.S. Cl.
CPC ............ *A61F 2/2433* (2013.01); *A61F 2/2418* (2013.01); *A61M 25/0136* (2013.01); *A61M 25/0147* (2013.01)
USPC ......................................... 623/2.11; 623/1.11

(58) Field of Classification Search
USPC ................ 623/1.11, 2.11; 606/191, 192, 194; 604/28, 93.01, 96.01, 500, 506, 507, 604/508; 128/897, 898
See application file for complete search history.

(56) References Cited

U.S. PATENT DOCUMENTS

| 4,378,224 A | 3/1983 | Nimni et al. |
| 4,473,067 A | 9/1984 | Schiff |

(Continued)

FOREIGN PATENT DOCUMENTS

| EP | 0815805 A2 | 1/1998 |
| EP | 941698 A1 | 9/1999 |

(Continued)

OTHER PUBLICATIONS

Lutter, M.D., et al., Percutaneous Valve Replacement: Current State and Future Prospects, Ann Thorac Sur 2004; 78:2199-2206.

(Continued)

*Primary Examiner* — Dianne Dornbusch
*Assistant Examiner* — Robert Lynch
(74) *Attorney, Agent, or Firm* — David Hauser; Guy Cumberbatch

(57) ABSTRACT

A delivery system and method for delivering a prosthetic heart valve to the aortic valve annulus. The system includes a delivery catheter having a steering mechanism thereon for delivering a balloon-expandable prosthetic heart valve to the aortic annulus in an antegrade fashion through an introducer passing into the left ventricle through its apex. The introducer may have a more floppy distal section than a proximal section to reduce trauma to the heart wall while preserving good operating field stability. The delivery catheter includes a deflecting segment just proximal to a distal balloon to facilitate positioning of the prosthetic heart valve in the proper orientation within the aortic annulus. A trigger in a catheter handle may be coupled to a deflection wire that actuates the deflecting segment, while a slider in the handle controls retraction of a valve pusher. The prosthetic heart valve may be installed over the existing calcified leaflets, and a pre-dilation valvuloplasty procedure may also be utilized.

14 Claims, 17 Drawing Sheets

(56) References Cited

U.S. PATENT DOCUMENTS

| | | | |
|---|---|---|---|
| 4,553,974 A | 11/1985 | Dewanjee | |
| 4,573,470 A | 3/1986 | Samson et al. | |
| 4,582,181 A | 4/1986 | Samson | |
| 4,605,002 A | 8/1986 | Rebuffat | |
| 4,647,283 A | 3/1987 | Carpentier et al. | |
| 4,648,881 A | 3/1987 | Carpentier et al. | |
| 4,753,652 A | 6/1988 | Langer et al. | |
| 4,944,740 A | 7/1990 | Buchbinder et al. | |
| 5,059,186 A | 10/1991 | Yamamoto et al. | |
| 5,125,895 A | 6/1992 | Buchbinder et al. | |
| 5,188,636 A | 2/1993 | Fedotov | |
| 5,304,184 A | 4/1994 | Hathaway et al. | |
| 5,306,234 A | 4/1994 | Johnson | |
| 5,318,587 A | 6/1994 | Davey | |
| 5,320,632 A | 6/1994 | Heidmueller | |
| 5,350,361 A | 9/1994 | Tsukashima et al. | |
| 5,364,408 A | 11/1994 | Gordon | |
| 5,368,601 A | 11/1994 | Sauer et al. | |
| 5,370,685 A | 12/1994 | Stevens | |
| 5,374,275 A | 12/1994 | Bradley et al. | |
| 5,403,329 A | 4/1995 | Hinchcliffe | |
| 5,417,699 A | 5/1995 | Klein et al. | |
| 5,417,700 A | 5/1995 | Egan | |
| 5,425,737 A | 6/1995 | Burbank et al. | |
| 5,431,666 A | 7/1995 | Sauer et al. | |
| 5,458,572 A | 10/1995 | Campbell et al. | |
| 5,527,322 A | 6/1996 | Klein et al. | |
| 5,537,322 A | 7/1996 | Denz et al. | |
| 5,545,214 A | 8/1996 | Stevens | |
| 5,571,215 A | 11/1996 | Sterman et al. | |
| 5,639,276 A | 6/1997 | Weinstock et al. | |
| 5,713,951 A | 2/1998 | Garrison et al. | |
| 5,792,152 A | 8/1998 | Klein et al. | |
| 5,792,172 A | 8/1998 | Fischell et al. | |
| 5,797,960 A | 8/1998 | Stevens et al. | |
| 5,810,850 A | 9/1998 | Hathaway et al. | |
| 5,820,631 A | 10/1998 | Nobles | |
| 5,860,990 A | 1/1999 | Nobles et al. | |
| 5,891,159 A | 4/1999 | Sherman et al. | |
| 5,924,424 A | 7/1999 | Stevens et al. | |
| 5,968,068 A | 10/1999 | Dehdashtian et al. | |
| 5,972,005 A | 10/1999 | Stalker et al. | |
| 6,013,092 A | 1/2000 | Dehdashtian et al. | |
| 6,033,378 A | 3/2000 | Lundquist et al. | |
| 6,071,273 A | 6/2000 | Euteneuer et al. | |
| 6,083,257 A | 7/2000 | Taylor et al. | |
| 6,106,540 A | 8/2000 | White et al. | |
| 6,117,144 A | 9/2000 | Nobles et al. | |
| 6,143,004 A | 11/2000 | Davis et al. | |
| 6,146,325 A | 11/2000 | Lewis et al. | |
| 6,206,893 B1 | 3/2001 | Klein et al. | |
| 6,231,563 B1 | 5/2001 | White et al. | |
| 6,245,079 B1 | 6/2001 | Nobles et al. | |
| 6,251,092 B1 | 6/2001 | Qin et al. | |
| 6,269,819 B1 | 8/2001 | Oz et al. | |
| 6,358,258 B1 | 3/2002 | Arcia et al. | |
| 6,379,372 B1 | 4/2002 | Dehdashtian et al. | |
| 6,419,643 B1 | 7/2002 | Shimada et al. | |
| 6,425,916 B1 | 7/2002 | Garrison et al. | |
| 6,454,777 B1 | 9/2002 | Green | |
| 6,506,339 B1 | 1/2003 | Girardot et al. | |
| 6,517,553 B2 | 2/2003 | Klein et al. | |
| 6,540,782 B1 | 4/2003 | Snyders | |
| 6,551,331 B2 | 4/2003 | Nobles et al. | |
| 6,558,418 B2 | 5/2003 | Carpentier et al. | |
| 6,562,052 B2 | 5/2003 | Nobles et al. | |
| 6,591,472 B1 | 7/2003 | Noone et al. | |
| 6,663,666 B1 | 12/2003 | Quiachon et al. | |
| 6,716,207 B2 | 4/2004 | Farnholtz | |
| 6,726,717 B2 | 4/2004 | Alfieri et al. | |
| 6,730,118 B2 | 5/2004 | Spenser et al. | |
| 6,733,509 B2 | 5/2004 | Nobles et al. | |
| 6,749,630 B2 | 6/2004 | McCarthy et al. | |
| 6,805,710 B2 | 10/2004 | Bolling et al. | |
| 6,821,297 B2 | 11/2004 | Snyders | |
| 6,858,039 B2 | 2/2005 | McCarthy | |
| 6,893,460 B2 | 5/2005 | Spenser et al. | |
| 6,899,704 B2 | 5/2005 | Sterman et al. | |
| 6,908,481 B2 | 6/2005 | Cribier | |
| 6,911,034 B2 | 6/2005 | Nobles et al. | |
| 6,976,991 B2 | 12/2005 | Hebert et al. | |
| 7,004,952 B2 | 2/2006 | Nobles et al. | |
| 7,078,163 B2 | 7/2006 | Torrianni | |
| 7,090,686 B2 | 8/2006 | Nobles et al. | |
| 7,100,614 B2 | 9/2006 | Stevens et al. | |
| 7,276,078 B2 | 10/2007 | Spenser et al. | |
| 7,294,148 B2 | 11/2007 | McCarthy | |
| 7,323,004 B2 | 1/2008 | Parihar | |
| 7,373,207 B2 | 5/2008 | Lattouf | |
| 7,377,926 B2 | 5/2008 | Topper et al. | |
| 7,462,191 B2 | 12/2008 | Spenser et al. | |
| 7,510,572 B2 | 3/2009 | Gabbay | |
| 7,513,908 B2 | 4/2009 | Lattouf | |
| 7,534,260 B2 | 5/2009 | Lattouf | |
| 7,611,535 B2 | 11/2009 | Woolfson et al. | |
| 7,780,723 B2 | 8/2010 | Taylor | |
| 7,803,167 B2 | 9/2010 | Nobles et al. | |
| 7,803,185 B2 | 9/2010 | Gabbay | |
| 7,905,892 B2 | 3/2011 | Nobles et al. | |
| 7,959,672 B2 | 6/2011 | Salahieh et al. | |
| 8,475,522 B2 | 7/2013 | Jimenez et al. | |
| 2001/0001812 A1 | 5/2001 | Valley et al. | |
| 2002/0173835 A1 | 11/2002 | Bourang et al. | |
| 2002/0177840 A1 | 11/2002 | Farnholtz | |
| 2003/0004460 A1 | 1/2003 | Bedell | |
| 2003/0085373 A1 | 5/2003 | Dehdashtian | |
| 2003/0109924 A1 | 6/2003 | Cribier | |
| 2004/0116956 A1 | 6/2004 | Duchamp et al. | |
| 2004/0199240 A1 | 10/2004 | Dorn | |
| 2004/0215139 A1 | 10/2004 | Cohen | |
| 2004/0260309 A1 | 12/2004 | Packard | |
| 2005/0043791 A1 | 2/2005 | McCarthy et al. | |
| 2005/0049698 A1 | 3/2005 | Bolling et al. | |
| 2005/0070844 A1 | 3/2005 | Chow et al. | |
| 2005/0075729 A1 | 4/2005 | Nguyen et al. | |
| 2005/0131533 A1 | 6/2005 | Alfieri et al. | |
| 2005/0137499 A1 | 6/2005 | Sheets et al. | |
| 2005/0148997 A1 | 7/2005 | Valley et al. | |
| 2005/0228407 A1 | 10/2005 | Nobles et al. | |
| 2005/0240200 A1 | 10/2005 | Bergheim | |
| 2005/0251251 A1 | 11/2005 | Cribier | |
| 2006/0004439 A1 | 1/2006 | Spenser et al. | |
| 2006/0041190 A1* | 2/2006 | Sato | 600/159 |
| 2006/0074484 A1 | 4/2006 | Huber | |
| 2006/0178675 A1 | 8/2006 | Hamman | |
| 2006/0195065 A1 | 8/2006 | Sakal et al. | |
| 2006/0195120 A1 | 8/2006 | Nobles et al. | |
| 2006/0212056 A1 | 9/2006 | Salvadori et al. | |
| 2006/0217803 A1 | 9/2006 | Ingle et al. | |
| 2006/0276889 A1 | 12/2006 | Chambers et al. | |
| 2006/0282102 A1 | 12/2006 | Nobles et al. | |
| 2006/0293745 A1 | 12/2006 | Carpentier et al. | |
| 2007/0005131 A1 | 1/2007 | Taylor | |
| 2007/0010829 A1 | 1/2007 | Nobles et al. | |
| 2007/0021828 A1 | 1/2007 | Krolik et al. | |
| 2007/0043385 A1 | 2/2007 | Nobles et al. | |
| 2007/0112422 A1 | 5/2007 | Dehdashtian | |
| 2007/0123979 A1 | 5/2007 | Perier et al. | |
| 2007/0149987 A1 | 6/2007 | Wellman et al. | |
| 2007/0203479 A1 | 8/2007 | Auth et al. | |
| 2007/0203506 A1 | 8/2007 | Sibbitt et al. | |
| 2007/0208550 A1 | 9/2007 | Cao et al. | |
| 2007/0250106 A1 | 10/2007 | Kim | |
| 2007/0276413 A1 | 11/2007 | Nobles | |
| 2007/0276414 A1 | 11/2007 | Nobles | |
| 2008/0004597 A1 | 1/2008 | Lattouf et al. | |
| 2008/0033459 A1 | 2/2008 | Shafi et al. | |
| 2008/0033476 A1 | 2/2008 | Greene | |
| 2008/0058839 A1 | 3/2008 | Nobles et al. | |
| 2008/0188873 A1 | 8/2008 | Speziali | |
| 2008/0269786 A1 | 10/2008 | Nobles et al. | |

(56) References Cited

U.S. PATENT DOCUMENTS

| | | |
|---|---|---|
| 2008/0312681 A1 | 12/2008 | Ansel et al. |
| 2009/0005757 A1 | 1/2009 | Taber |
| 2009/0069887 A1 | 3/2009 | Righini et al. |
| 2009/0099578 A1 | 4/2009 | Heneveld et al. |
| 2009/0240264 A1 | 9/2009 | Tuval et al. |
| 2009/0287182 A1 | 11/2009 | Bishop et al. |
| 2009/0287183 A1 | 11/2009 | Bishop et al. |
| 2010/0030242 A1 | 2/2010 | Nobles et al. |

FOREIGN PATENT DOCUMENTS

| | | |
|---|---|---|
| EP | 1 356 793 A2 | 10/2003 |
| EP | 1447111 A1 | 8/2004 |
| EP | 1570790 A2 | 9/2005 |
| EP | 2114318 A1 | 11/2009 |
| EP | 2120794 A1 | 11/2009 |
| WO | WO-9413211 A1 | 6/1994 |
| WO | WO-95/03742 A1 | 2/1995 |
| WO | WO-9513021 A1 | 5/1995 |
| WO | 96/30073 A1 | 10/1996 |
| WO | WO-96/40347 A1 | 12/1996 |
| WO | WO-9903904 A1 | 1/1999 |
| WO | WO-0108050 A1 | 2/2001 |
| WO | WO-0126724 A2 | 4/2001 |
| WO | WO-2005034801 A2 | 4/2005 |
| WO | WO-2005102015 A2 | 11/2005 |
| WO | WO-2006019798 A1 | 2/2006 |
| WO | WO-2006023676 A1 | 3/2006 |
| WO | WO-2006041505 A1 | 4/2006 |
| WO | WO-2006091597 A1 | 8/2006 |
| WO | WO-2006/127765 A1 | 11/2006 |
| WO | WO-2006/138173 A2 | 12/2006 |
| WO | WO-2007002920 A2 | 1/2007 |
| WO | WO-2008058519 A1 | 5/2008 |
| WO | 2008138584 A1 | 11/2008 |

OTHER PUBLICATIONS

Shanebrook, PhD., et al., Hemodynamics of Left Ventricular Apex-Aortic Valved Conduits, Cardiovascular Diseases, Bulletin of the Texas Heart Institute, vol. 6, No. 4, Dec. 1979.
Zhou, et al., Self-Expandable Valved Stent of Large Size: Off-Bypass Implantation in Pulmonary Position, European Journal of Cardio-Thoracic Surgery 24 (2003) 212-216.
Brodsky, Adam M., Percutaneous Approaches to Aortic Valve Replacement, SCAI, <http://www.scai.org/pdf/AR__12-04__SCAI__Brodsky.pdf>, Dec. 2004.
*Pioneering Techniques in Cardiac Surgery, The Fourth in the Series*, Program Flyer, Heart Center Leipzig Auditorium, Leipzig, German, Dec. 1-2, 2005.
Todd M. Dewey, et al., Feasibility of a Trans-Apical Approach for Aortic Valve Implantation Using a Device Delivered Valve, AbstractPresentation at ISMICS 8.sup.th Annual Meeting , Jun. 1-4, 2005 New York (pp. 1-2—of flier also attached).
Liang Ma, et al., Double-crowned valved stents for off-pump mital valve repalcement, European Journal of Cardio-Thoracic Surgery 28 (2005) pp. 194-199.
F. L. Wellens, How Long Will the Heart Still Beat?, Texas Heart Institute Journal, vol. 32, No. 2, 2005, pp. 126-129.
Christoph H. Huber, et al., Direct-Access Valve Replacement a Novel Approach for Off-Pump Valve Implantation Using Valved Stents, JACC, vol. 46, No. 2, 2005, pp. 366-370, www.content.onlinejacc.org by Susan Porter on Sep. 27, 2005.
Kevin A. Greer, et al., Skeletal Muscle Ventricles, Left Ventricular Apex-to-Aorta Configuration: 1-11 Weeks in Circulation, Circulation 95: 497-502.
Ferrari, M., et al., Transarterial Aortic Valve Replacement With a Self-Expanding Stent in Pigs. Heart 2004 90: 1326-1331.
Brodsky, Adam M., Percutaneous Approaches to Aortic Valve Replacement, SCA1, <http://www.scai.org/pdf/AR.sub.--12-04.sub.--SCAI.sub.--Brodsky-.pdf>, Dec. 2004.
Hungarian Search Report, Oct. 31, 2013.

\* cited by examiner

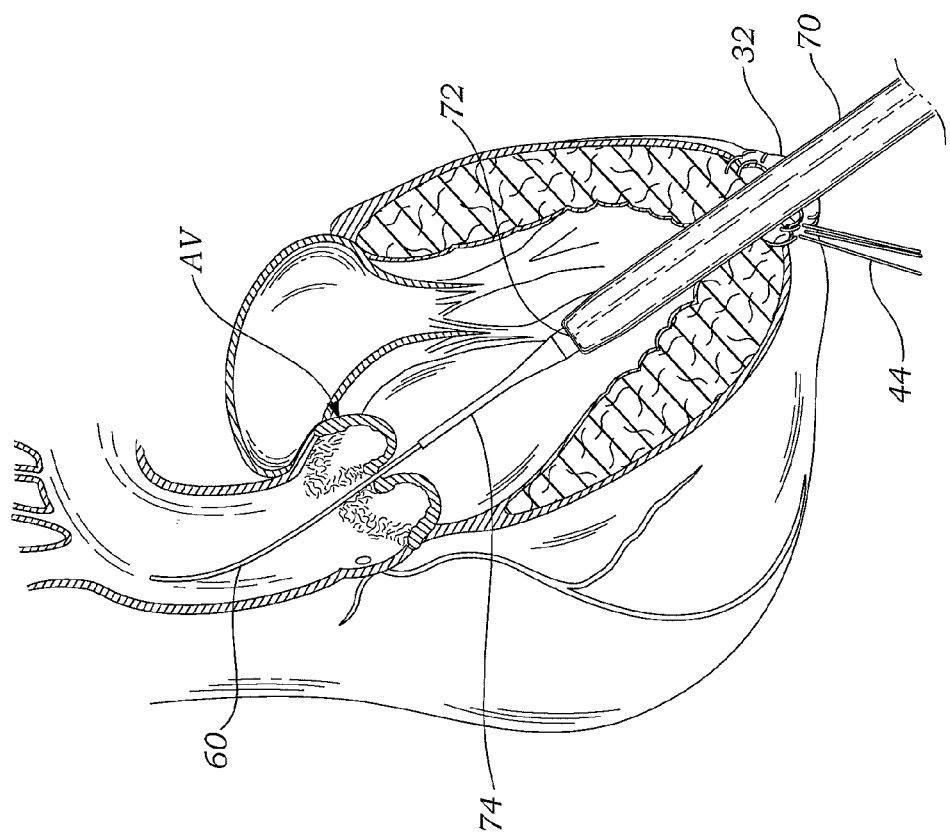

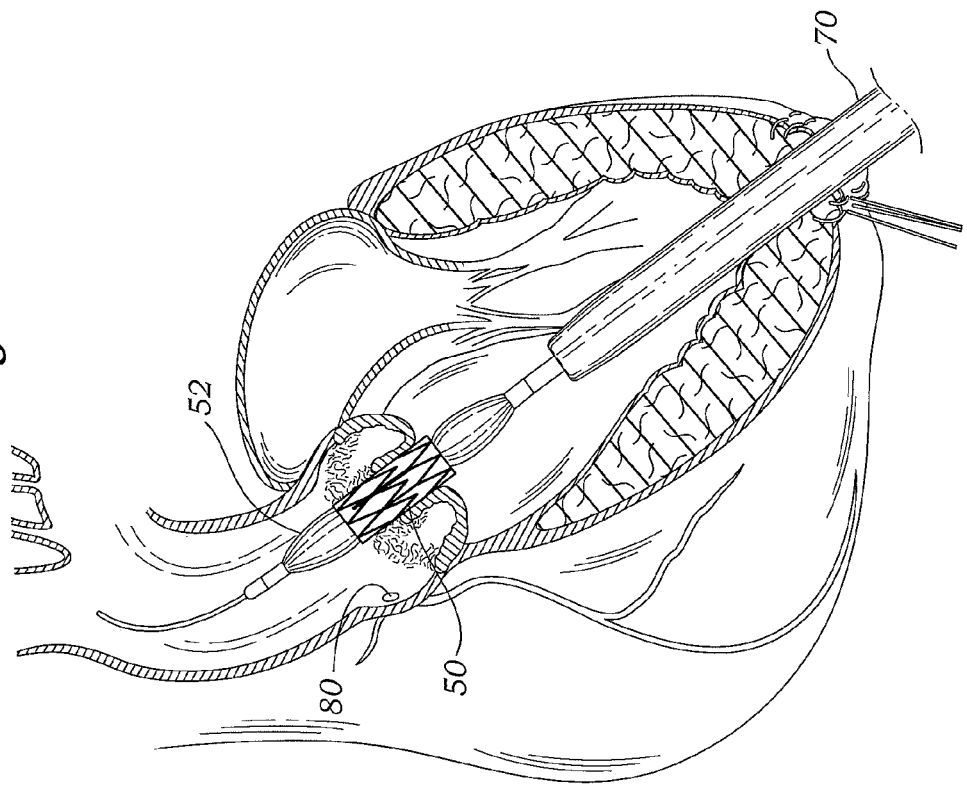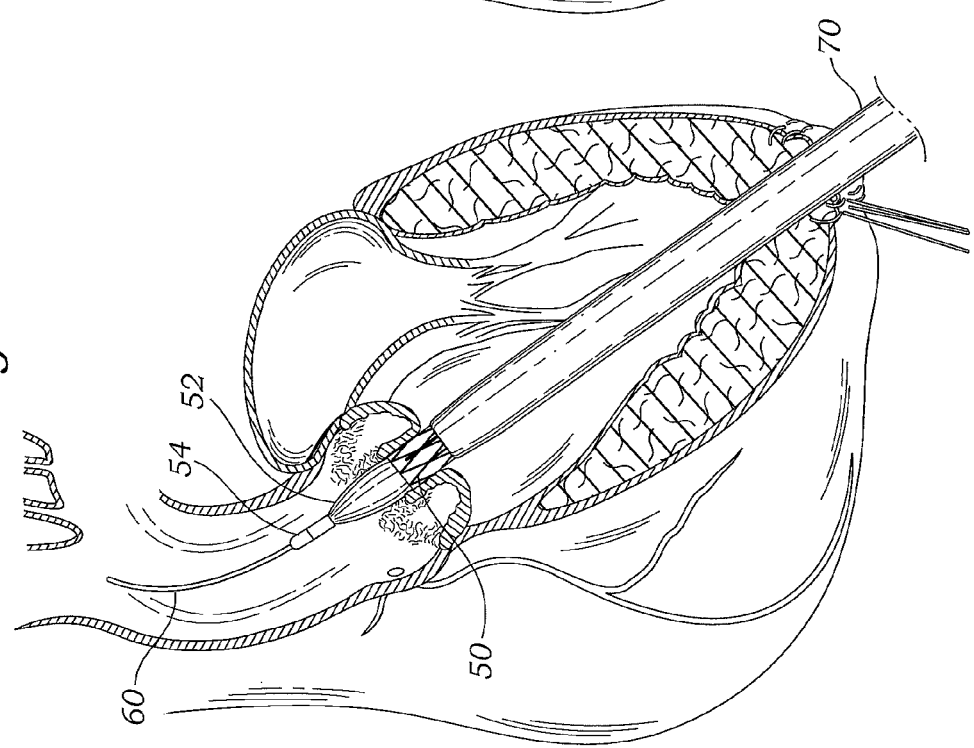

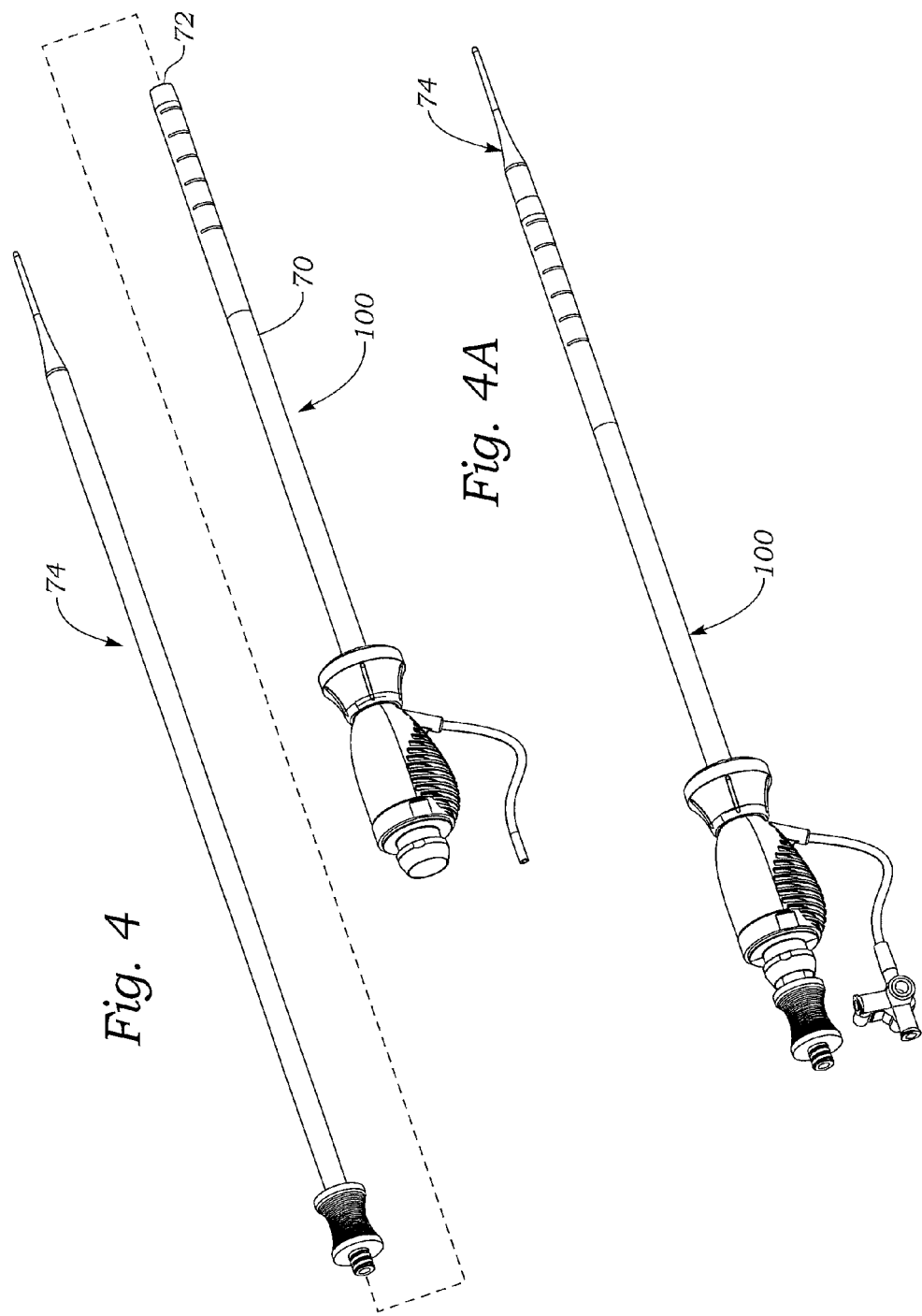

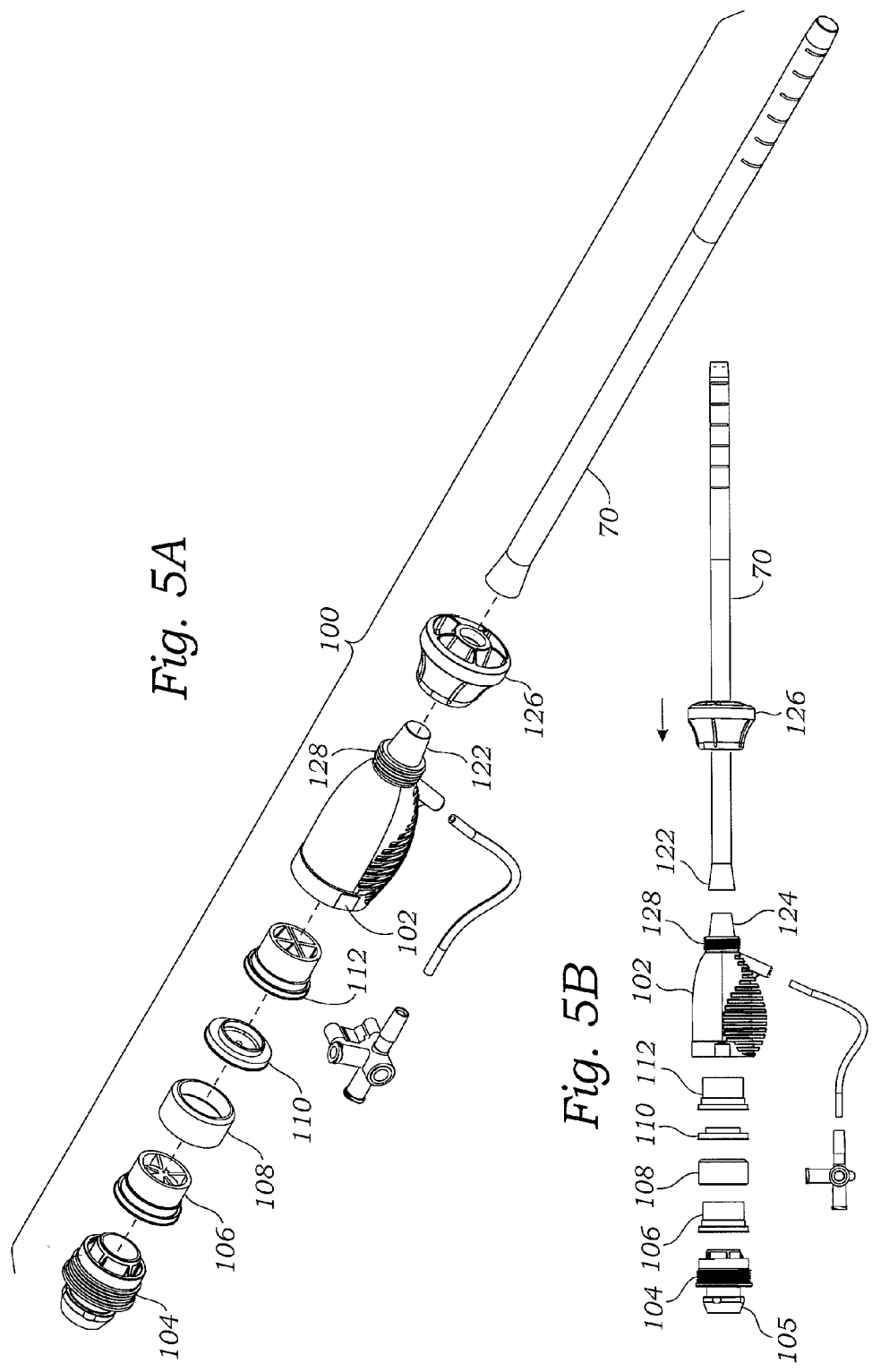

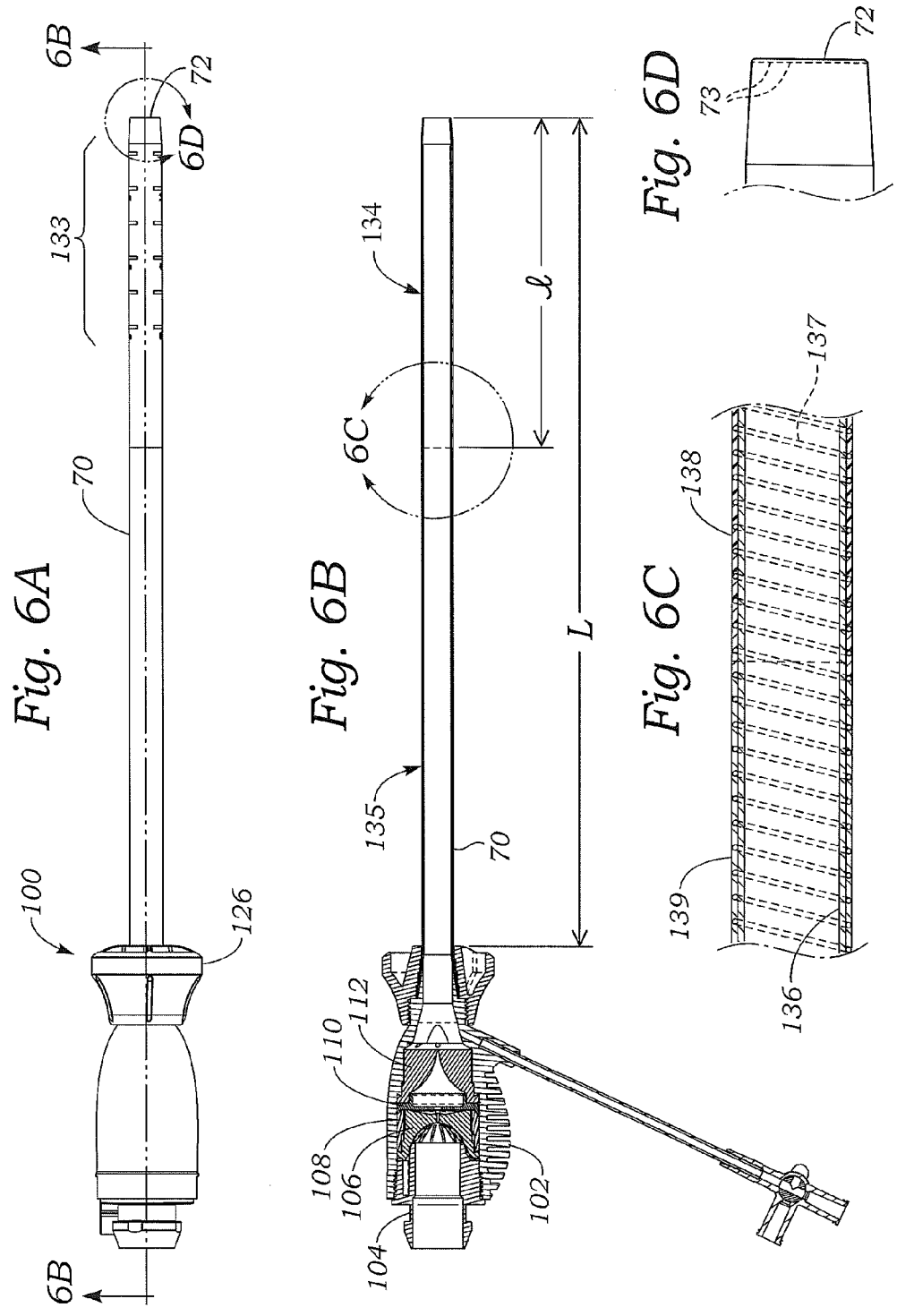

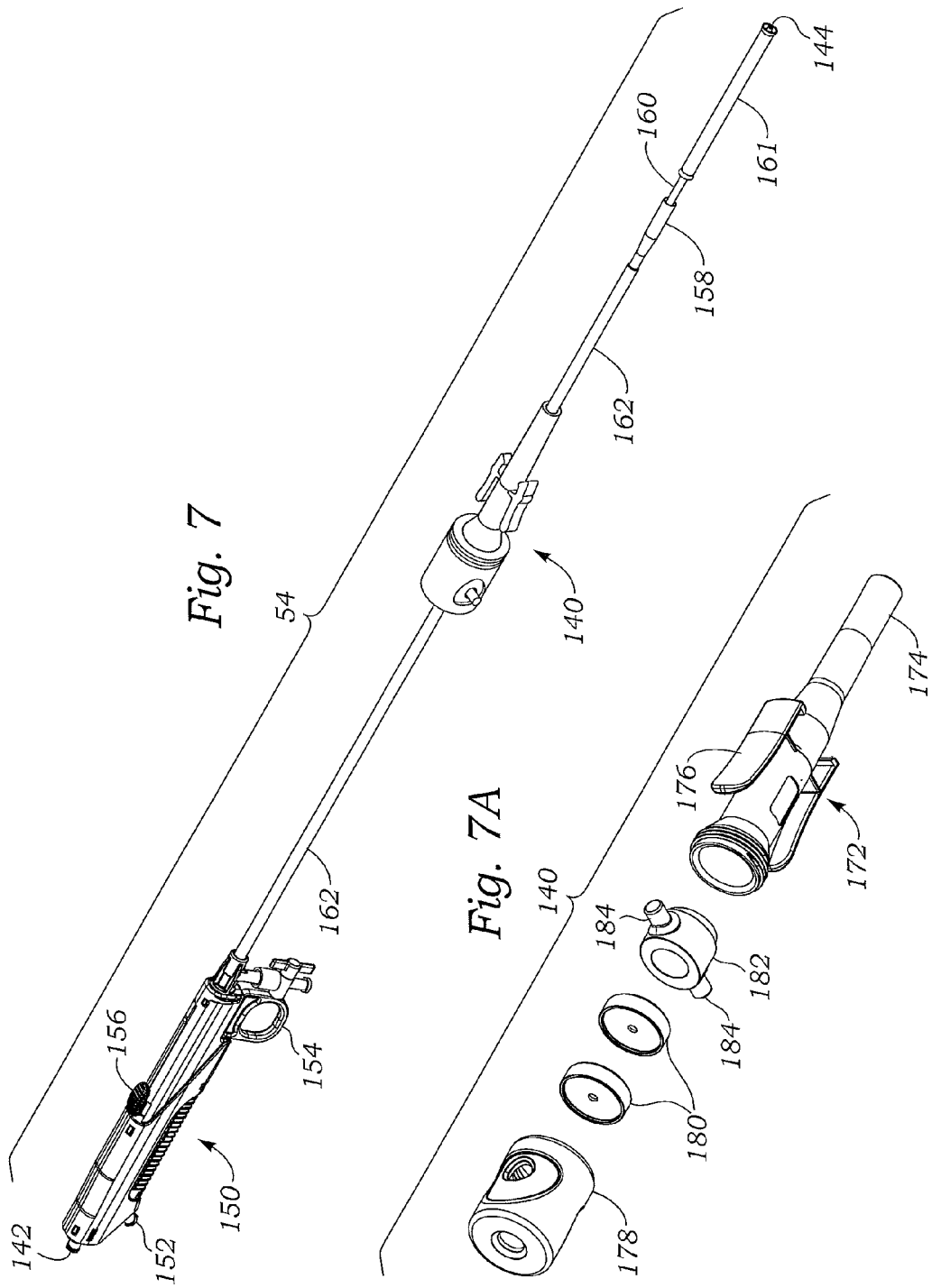

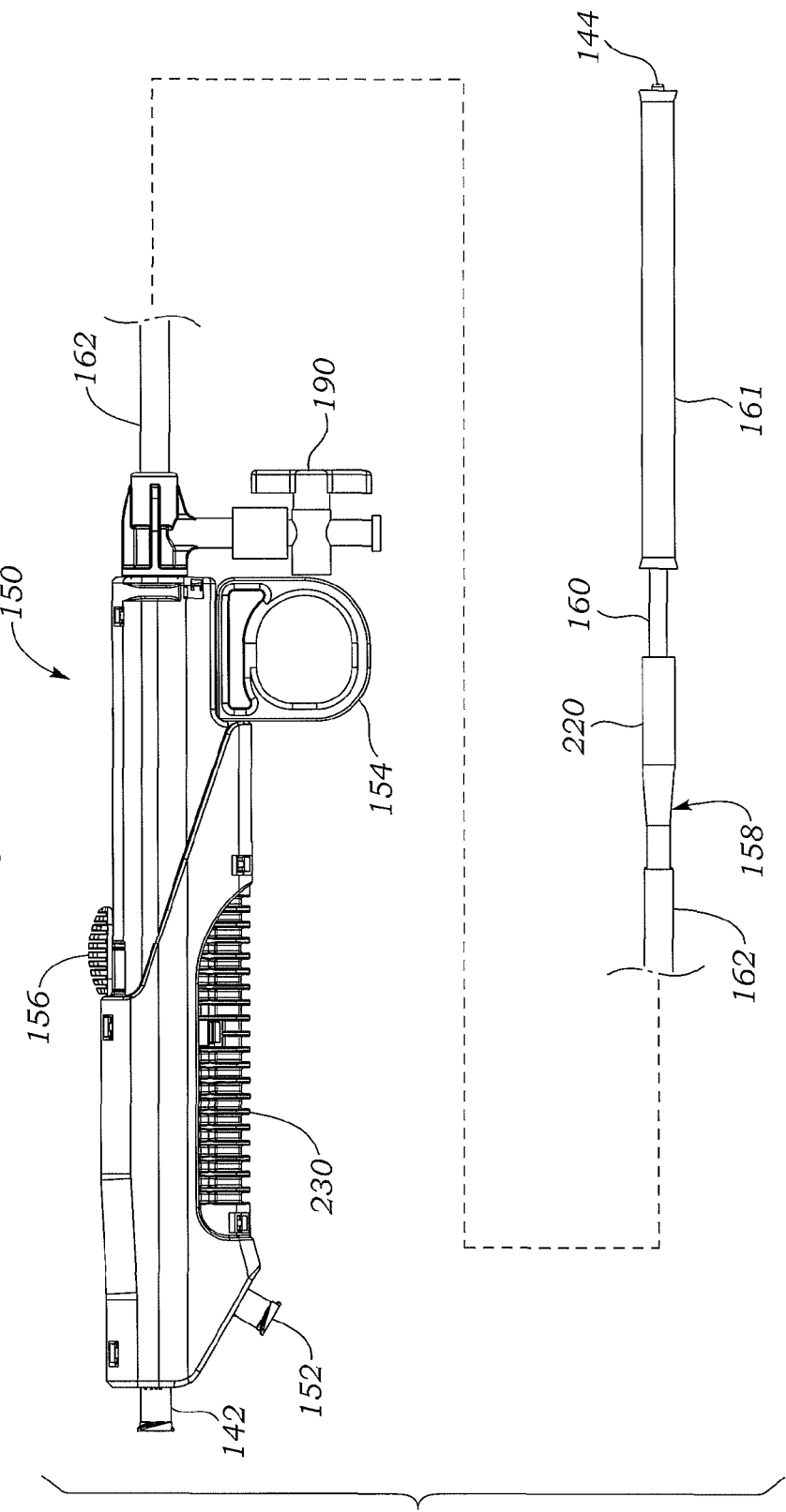

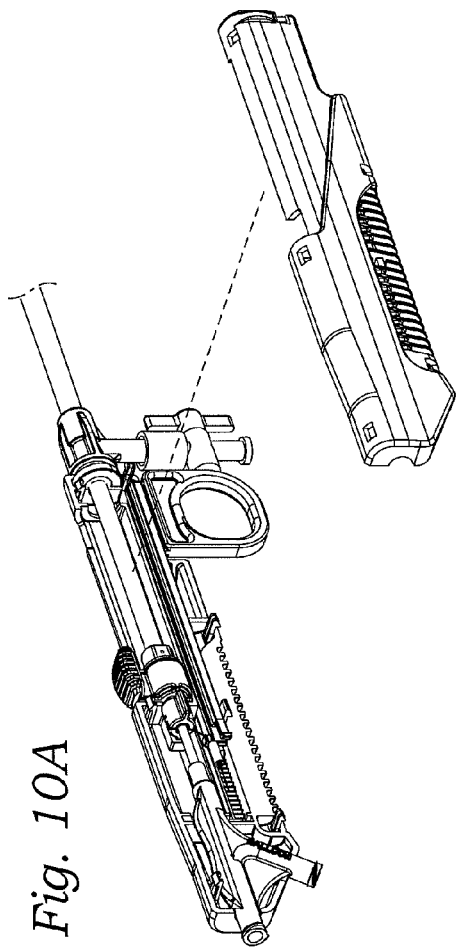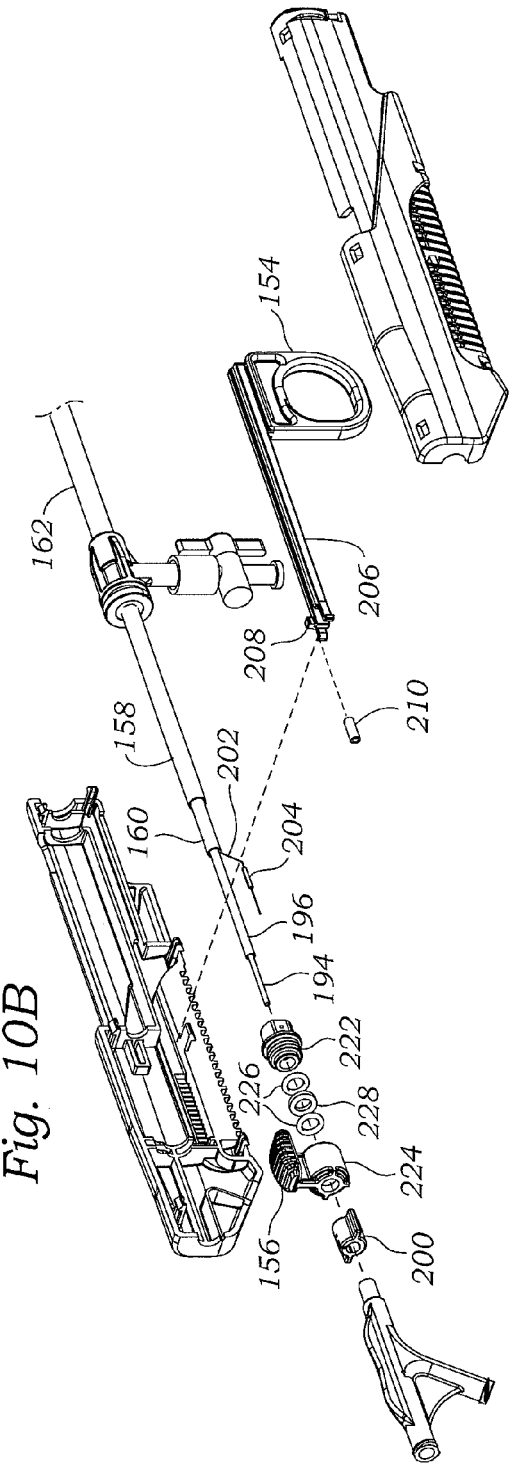

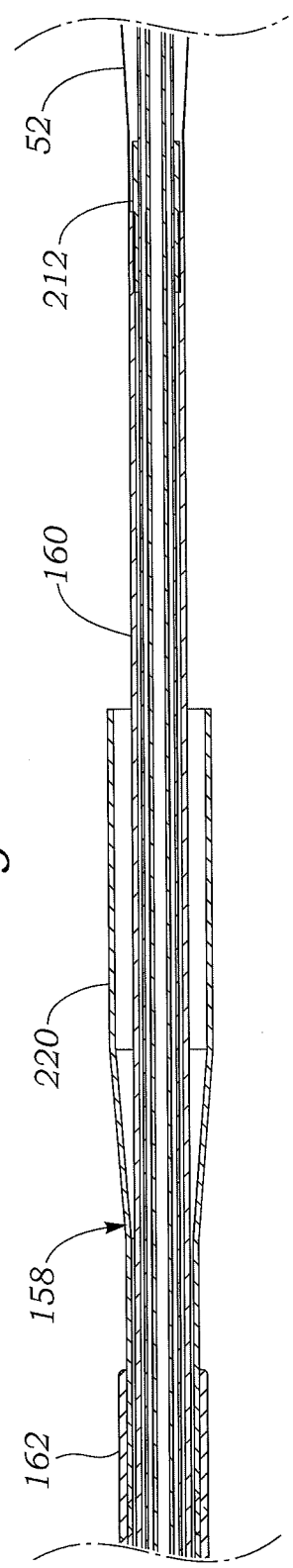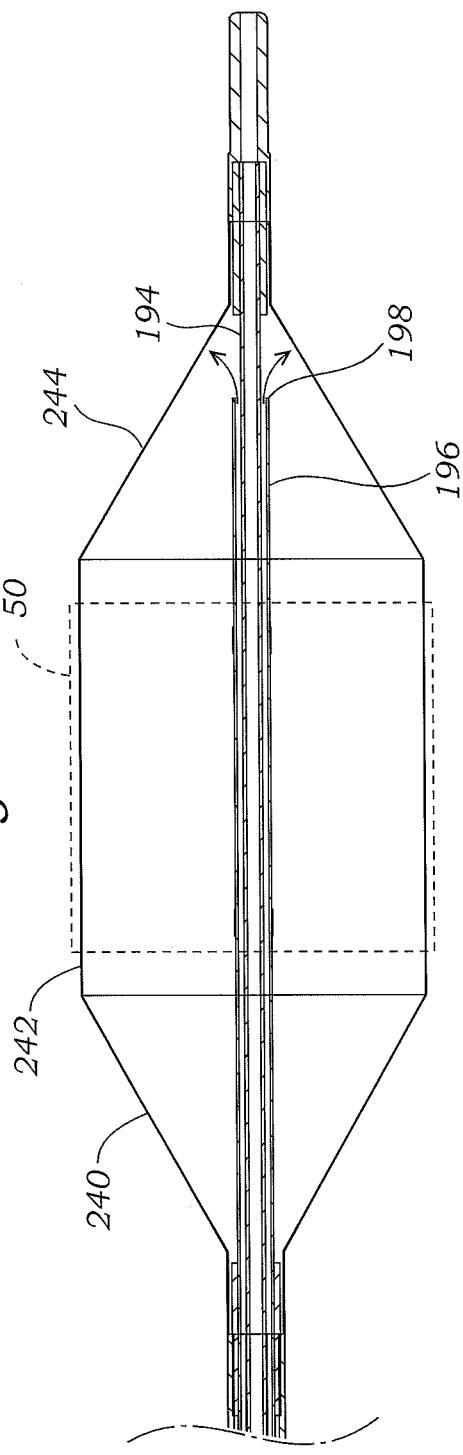

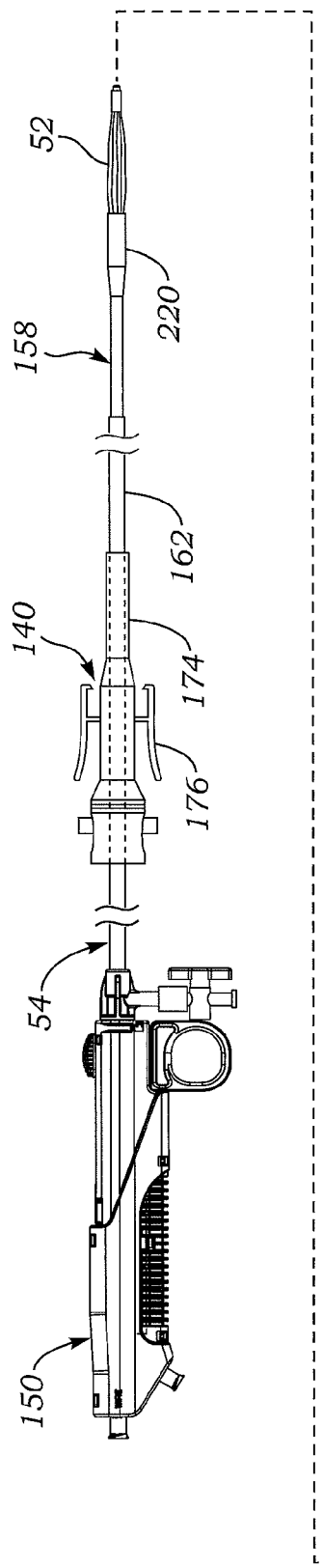
Fig. 13
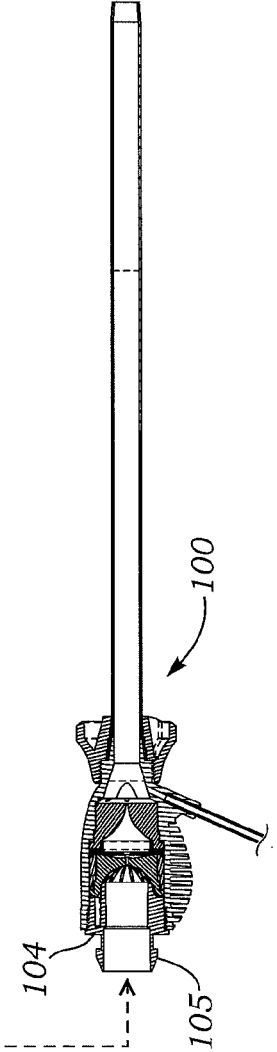
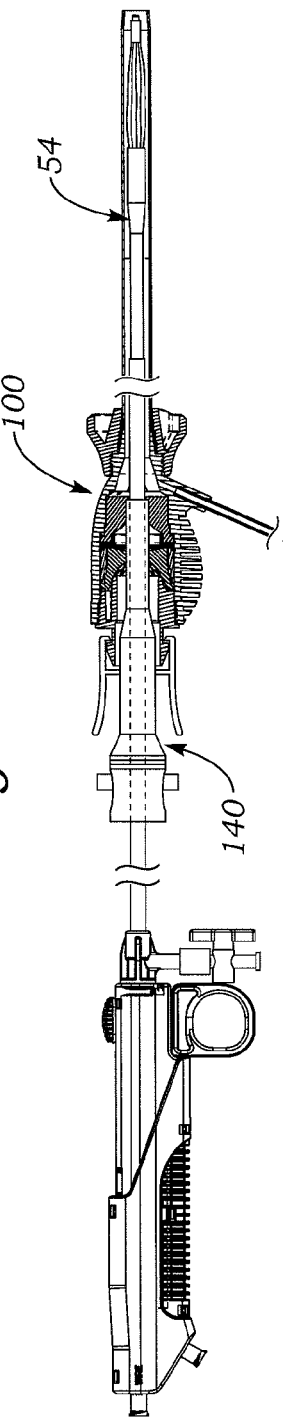
Fig. 14A

METHODS OF VALVE DELIVERY ON A BEATING HEART

RELATED APPLICATIONS

The present application is a continuation of U.S. application Ser. No. 12/835,546, filed Jul. 13, 2010, now U.S. Pat. No. 8,475,522, which claims priority under 35 U.S.C. §119(e) to U.S. provisional application No. 61/225,510 filed Jul. 14, 2009.

FIELD OF THE INVENTION

The present invention relates to methods and systems used to deliver a prosthetic valve to a heart. More specifically, the present invention relates to methods and apparatus for surgically replacing a heart valve without opening the chest cavity and with or without placing the patient on bypass, the latter being termed "off-pump."

BACKGROUND OF THE INVENTION

Heart valve replacement may be indicated when there is a narrowing of the native heart valve, commonly referred to as stenosis, or when the native valve leaks or regurgitates, such as when the leaflets are calcified. When replacing the valve, the native valve may be excised and replaced with either a biologic or a mechanical valve. Mechanical valves require lifelong anticoagulant medication to prevent blood clot formation, and clicking of the valve often may be heard through the chest. Biologic tissue valves typically do not require such medication. Tissue valves may be obtained from cadavers or may be porcine or bovine, and are commonly attached to cloth-covered synthetic rings and/or leaflet support frames that are secured to the patient's heart valve annulus.

Conventional heart valve surgery is an open-heart procedure conducted under general anesthesia. An incision is made through the patient's sternum (sternotomy), and the patient's heart is stopped while blood flow is rerouted through a heart-lung "cardiopulmonary" bypass machine. Valve replacement surgery is a highly invasive operation with significant concomitant risks include bleeding, infection, stroke, heart attack, arrhythmia, renal failure, adverse reactions to the anesthesia medications, as well as sudden death. Fully 2-5% of patients die during surgery. Post-surgery, patients temporarily may be confused due to emboli and other factors associated with the heart-lung machine. The first 2-3 days following surgery are spent in an intensive care unit where heart functions can be closely monitored. The average hospital stay is between 1 to 2 weeks, with several more weeks to months required for complete recovery.

In recent years, advancements in "minimally-invasive" surgery and interventional cardiology have encouraged some investigators to pursue percutaneous replacement of the aortic heart valve. Percutaneous Valve Technologies ("PVT"), formerly of Fort Lee, N.J. and now part of Edwards Lifesciences of Irvine, Calif., has developed a plastically- or balloon-expandable stent integrated with a bioprosthetic valve. The stent/valve device, now called the Edwards Sapien™ Heart Valve, is deployed across the native diseased valve to permanently hold the valve open, thereby alleviating a need to excise the native valve. The Edwards Sapien™ Heart Valve is designed for delivery in a cardiac catheterization laboratory under local anesthesia using fluoroscopic guidance, thereby avoiding general anesthesia and open-heart surgery. The Sapien™ Heart Valve may be inserted trans-femorally with the RetroFlex™ delivery system, or transapically with the Ascendra™ delivery system. A description of the Ascendra™ delivery system is provided in U.S. Patent Publication No. 2007-0112422 to Dehdashtian.

Other prior art minimally-invasive heart valves use self-expanding stents as anchors. In the percutaneous/endovascular aortic valve replacement procedure, accurate placement of the prosthetic valve relative to the coronary ostia is critical. Though the proximal end of the stent is not released from the delivery system until accurate placement is verified by fluoroscopy, the self-expanding stent may still jump once released. It is therefore often difficult to know where the ends of the stent will be with respect to the native valve and surrounding structures.

U.S. Pat. No. 6,425,916 to Garrison et al. describes a two-piece device for replacement of the aortic valve that is adapted for delivery through a patient's aorta. A stent is endovascularly placed across the native valve, then a replacement valve is positioned within the lumen of the stent and connected thereto. By separating the stent and the valve during delivery, a so-called "two-stage" approach, the profile of the delivery system can be reduced. Both the stent and a frame of the replacement valve may be balloon- or self-expandable.

Some researchers propose implanting prosthetic heart valves at the aortic annulus through a ventricular approach. For instance, Christoph H. Huber of the Brigham and Women's Hospital of Harvard Medical School, and others, have proposed a procedure in which a self-expanding valve stent is implanted at the aortic position using a direct-access transapical approach. (E.g., Huber, et al. Direct-access valve replacement a novel approach for off-pump valve implantation using valved stents. J Am Coll Cardiol 2005; 46:366-70). The clinical studies by Huber, et al. recommend use of the procedure only for animals with normal, noncalcified leaflets. More recently, Bergheim in U.S. Patent Publication No. 2005/0240200 discloses another transapical approach in which either a balloon- or self-expanding valve may be implanted, and also proposes removing or decalcifying stenotic valves. Such direct-access or "port access" techniques though less invasive than conventional open heart surgery are not called, "minimally-invasive," as that term is now primarily used to refer to valves delivered using elongated catheters via the vasculature (i.e., endovascularly).

In view of drawbacks associated with previously known techniques for replacing a heart valve without open-heart surgery or cardiopulmonary bypass, i.e., minimally-invasive procedures, improved methods and apparatuses that are more robust and even less invasive are needed.

SUMMARY OF THE INVENTION

Preferred embodiments of the present invention provide a heart valve delivery system for delivery of a prosthetic (i.e., replacement) heart valve to a native valve site without an open chest procedure. The delivery system includes a valve delivery catheter having a steerable section to facilitate positioning of the valve.

In accordance with one embodiment of the present application, a medical catheter introducer includes an elongated tubular sheath extending distally from a proximal housing and containing at least one introducer valve for fluidly sealing around a catheter. The sheath has a proximal segment with a first stiffness extending a length L of at least one half the length of the sheath, and a distal section with a second stiffness less than the first stiffness and having a length l. Desirably, the length l of the distal section ranges between about 4-12 cm. In one embodiment, the length L of the proximal segment is at least 24 cm, and the length l of the distal section ranges between about 6-9 cm. Also, the tubular sheath may have an inner liner and a reinforcing coil that both extend the entire length, and at least two sections of outer tubes in series having different durometers that create the differing stiffnesses of the sheath.

Another aspect disclosed herein is a medical introducer and heart valve delivery catheter combination comprising a delivery catheter having a distal balloon of sufficient diameter to expand a crimped heart valve thereon. An introducer that receives the delivery catheter therethrough has an elongated tubular sheath extending distally from a proximal housing. The proximal housing contains at least one introducer valve for fluidly sealing around a proximal length of the delivery catheter. The sheath further includes a proximal segment with a first stiffness extending a length L of at least one half the length of the sheath, and a distal section with a second stiffness different than the first stiffness and a length l. A tubular loader defines a throughbore that receives a distal portion of the delivery catheter, the tubular loader having structure for engaging mating structure on a proximal end of the introducer housing and a distal nose that extends through and opens the introducer valve and facilitates passage therethrough of the balloon of the delivery catheter.

A still further feature of the present application is a medical introducer and heart valve delivery catheter combination, comprising a delivery catheter having a distal balloon of sufficient diameter to expand a crimped heart valve thereon. The catheter includes a marker band at a proximal end of the balloon, and a tubular valve pusher that moves longitudinally with respect to the balloon and has a distal marker band. An introducer having an elongated tubular sheath extending distally from a proximal housing contains at least one introducer valve for fluidly sealing around a proximal length of the delivery catheter. The introducer sheath has a throughbore for passage of the delivery catheter and a marker dot array around its distal tip to distinguish the distal tip from the marker bands of the balloon and the pusher.

In accordance with a still further aspect, a medical introducer and heart valve delivery catheter combination comprises a delivery catheter, an introducer, and a tubular loader therebetween. The delivery catheter has a distal balloon of sufficient diameter to expand a crimped heart valve thereon. The introducer has an elongated tubular sheath extending distally from a proximal housing which contains at least one introducer valve for fluidly sealing around a proximal length of the delivery catheter. Finally, the tubular loader includes a throughbore that receives a distal portion of the delivery catheter, structure for engaging mating structure on a proximal end of the introducer housing, and a distal nose that extends through and opens the introducer valve, facilitating passage therethrough of the balloon of the delivery catheter. The loader also has a proximal housing with a seal for fluidly sealing around the introducer sheath, and a single-handed vent for aspirating air from within the loader.

A heart valve delivery catheter of the present application includes a catheter tube having a distal balloon thereon of sufficient diameter to fully expand a crimped heart valve from within. The balloon is disposed on the end of a deflectable portion of the catheter tube actuated by a deflection pull wire. The delivery catheter further includes a tubular valve pusher that slides over the catheter tube and moves longitudinally with respect to the balloon. The delivery catheter also has a proximal control handle on which are mounted both a deflection actuator for deflecting the deflectable portion of the catheter tube and a pusher actuator for displacing the valve pusher. Preferably, the delivery catheter includes a plurality of concentric tubes extending from within the control handle, and at least one passive seal within the handle for sealing around one of the tubes without preventing its movement.

Another benefit of the present application is a medical introducer and heart valve delivery catheter combination that comprises a delivery catheter having a catheter tube with a distal balloon thereon of sufficient diameter to fully expand a crimped heart valve from within. An introducer has an elongated tubular sheath extending distally from a proximal housing which contains at least one introducer valve for fluidly sealing around a proximal length of the delivery catheter. A tubular loader defines a throughbore that receives a distal portion of the delivery catheter, and includes structure for engaging mating structure on a proximal end of the introducer housing and a distal nose that extends through and opens the introducer valve and facilitates passage therethrough of the balloon of the delivery catheter. The loader has a proximal housing with a loader seal for fluidly sealing around the introducer sheath, and a single-handed vent for aspirating air from within the loader.

A heart valve delivery catheter and heart valve combination disclosed herein features an expandable prosthetic heart valve having a crimped configuration and proximal and distal ends. A delivery catheter includes a catheter tube with a distal balloon thereon of sufficient diameter to fully expand the crimped heart valve from within. The balloon has a length greater than the length of the heart valve so as to have proximal and distal exposed portions, and the balloon is folded in a manner that leaves only longitudinal fold lines to contrast with the ends of the heart valve under echocardiography.

A heart valve delivery catheter of the present application a delivery catheter having a catheter tube with a distal balloon thereon of sufficient diameter to fully expand the crimped heart valve from within, the balloon being disposed on the end of a deflection tube actuated by a deflection pull wire, the deflectable portion comprising a braided structure and the deflection wire extending along its length up to a distal coil to which the deflection wire attaches, the deflectable portion having a dimension no greater than 8 French.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

Features and advantages of the present invention will become appreciated as the same become better understood with reference to the specification, claims, and appended drawings wherein:

FIGS. 3A-3E are cross-sectional views through the left side of a patient's heart showing several steps in a procedure for implanting a prosthetic heart valve in accordance with the present invention;

FIG. 4 is an exploded perspective view of an introducer/dilator combination used in the port access heart valve implantation procedure of the present invention;

FIG. 4A is an assembled view of the introducer/dilator combination of FIG. 4;

FIGS. 5A and 5B are exploded perspective and elevational views of the introducer of FIG. 4;

FIG. 6A is a plan view of the introducer of FIG. 4;

FIG. 6B is a longitudinal sectional view of the introducer taken along line 6B-6B of FIG. 6A;

FIGS. 6C and 6D are enlarged views portions of a variable flexibility sheath of the introducer of FIG. 6B;

FIG. 7 is a perspective view of an exemplary balloon catheter/loader assembly for implanting a prosthetic heart valve as disclosed herein;

FIG. 7A is an exploded perspective view of a loader that provides an interface between the introducer of FIGS. 4-6 and the balloon catheter of FIG. 7;

FIG. 8 is a broken elevational view of the balloon catheter of FIG. 7;

FIGS. 10A and 10B are exploded views of the proximal control handle of FIG. 9;

FIG. 11 is an enlarged sectional view of a distal deflecting segment of the balloon catheter of FIG. 7, also showing a distal balloon in a deflated state within a protective sheath;

FIG. 12 is an enlarged sectional view of a distal balloon of the balloon catheter of FIG. 7 in its inflated state;

FIG. 13 is an exploded view of the balloon catheter and introducer (in section) combination prior to coupling with a heart valve crimped onto the balloon;

FIG. 14A is an assembled view of the balloon catheter and introducer (in section) combination after insertion of the balloon catheter through the introducer;

DETAILED DESCRIPTION OF THE PREFERRED EMBODIMENTS

The heart is a hollow muscular organ of a somewhat conical form; it lies between the lungs in the middle mediastinum and is enclosed in the pericardium. The heart rests obliquely in the chest behind the body of the sternum and adjoining parts of the rib cartilages, and projects farther into the left than into the right half of the thoracic cavity so that about one-third is situated on the right and two-thirds on the left of the median plane. The heart is subdivided by septa into right and left halves, and a constriction subdivides each half of the organ into two cavities, the upper cavity being called the atrium, the lower the ventricle. The heart therefore consists of four chambers; the right and left atria, and right and left ventricles.

Figure 1:
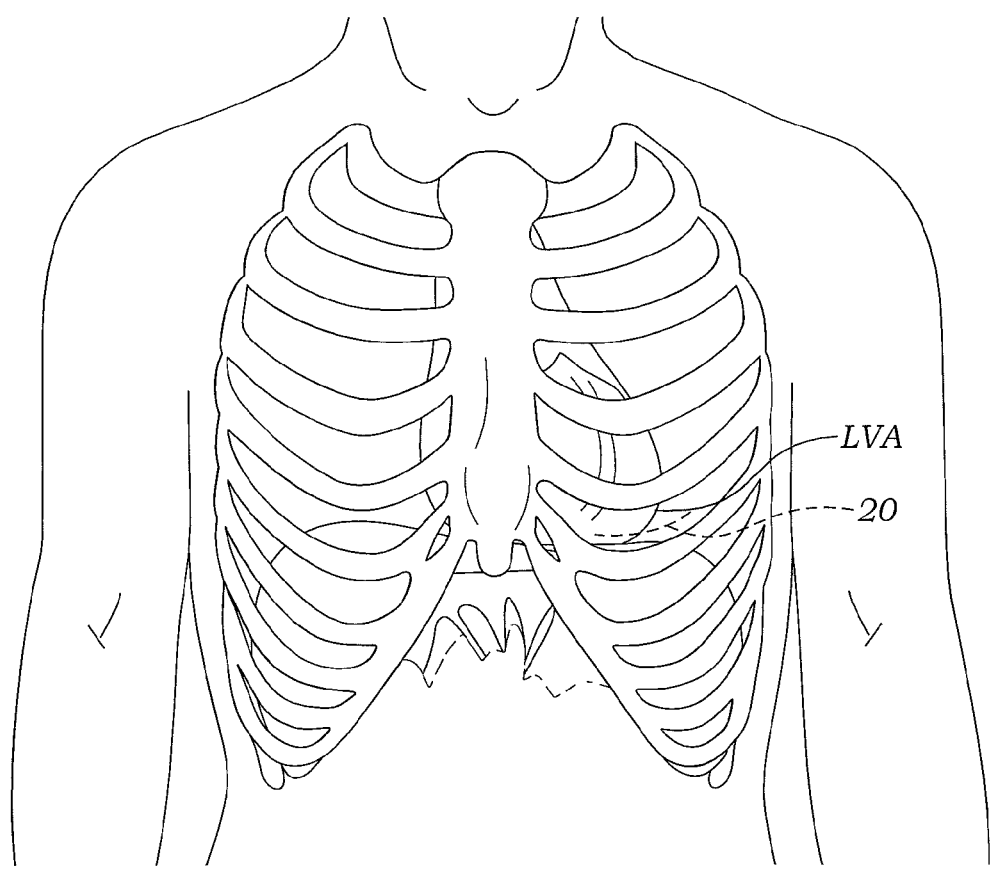
FIG. 1 is a schematic frontal view of a patient showing the location of an intercostal incision providing access to the apex of the left ventricle of the heart.

As seen in FIG. 1, the left ventricular apex LVA is directed downward, forward, and to the left (from the perspective of the patient). The apex typically lies behind the fifth left intercostal space (or between the fourth and fifth), 8 to 9 cm from the mid-sternal line, and about 4 cm below and 2 mm to the medial side of the left mammary papilla. Access to the left ventricle may therefore be attained through an intercostal incision 20 as shown in dashed line, positioned over the fifth left intercostal space. Such an approach is often termed a "mini-thoracotomy," and lends itself to surgical operations on the heart carried out using one or more short tubes or "ports"—thus, the operations are often referred to as "port-access" procedures.

In a preferred embodiment of the present invention, a surgeon implants a prosthetic heart valve over the existing native leaflets, which are typically calcified. There are procedures and devices for removing calcified leaflets, but the risks associated therewith, including a release of calcific material into the bloodstream, are not insignificant. Therefore, a heart valve replacement procedure that installs the prosthetic heart valve directly over and contains the native leaflets is preferred.

Figure 2B:
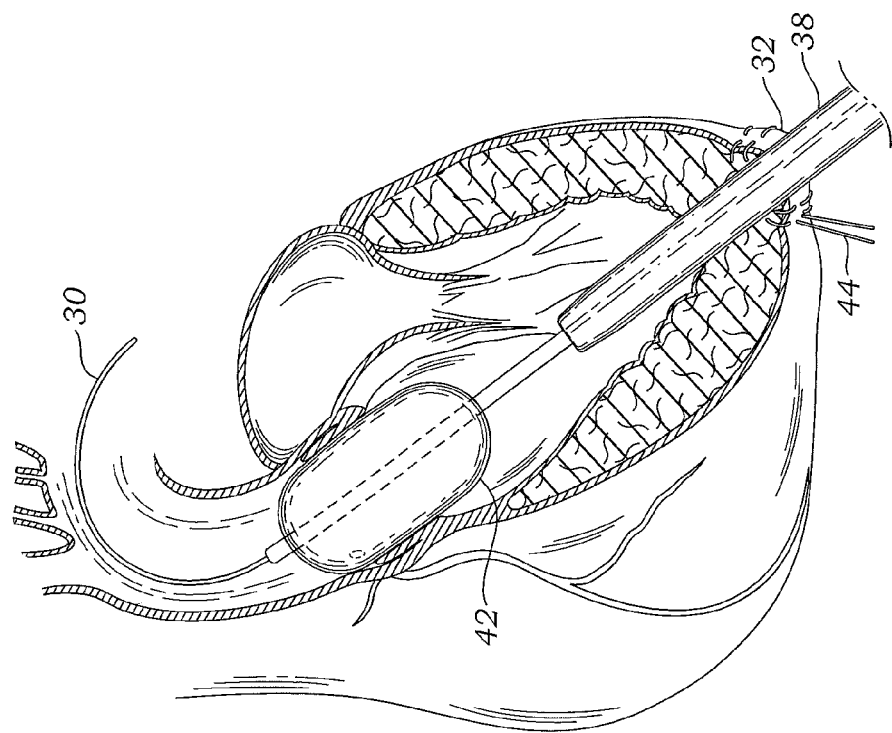
FIGS. 2A-2B are cross-sectional views through the left side of a patient's heart showing a procedure for dilating a calcified aortic annulus prior to implantation of a prosthetic heart valve in accordance with the present invention.
Figure 2A:
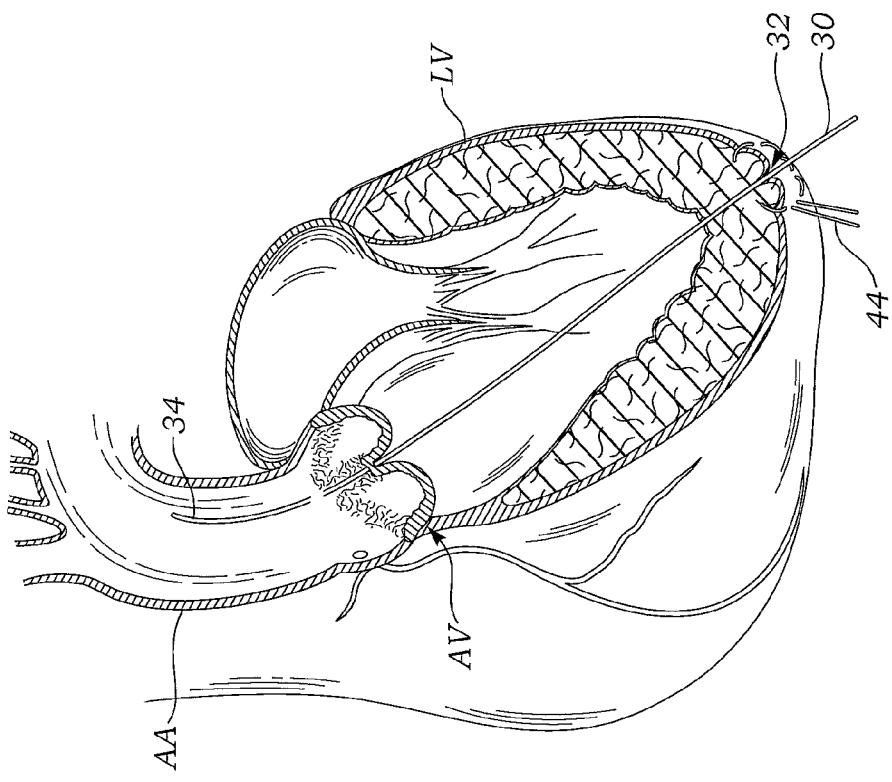

Those skilled in the art will recognize that it may be necessary to pre-dilate the leaflets and annulus of the stenotic aortic valve before deploying a prosthetic valve within the aortic valve. FIGS. 2A and 2B are two snapshots of a valvuloplasty procedure that may be initially performed to compress the native aortic heart valve leaflets outward against the sinuses and ascending aorta. As mentioned above, the native aortic valve leaflets may be substantially calcified, and the valvuloplasty may be necessary to crack and otherwise force apart hardened tissue. Pre-dilation increases the flow area through the aortic valve and creates an opening in the leaflets of sufficient size to receive the prosthetic valve. Pre-dilatation is preferably achieved using an expandable member, such as a dilatation balloon catheter. One example of pre-dilation of a valve annulus is seen in U.S. Pat. No. 6,908,481 to Cribier, issued Jun. 21, 2005 and expressly incorporated by reference herein.

FIG. 2A illustrates introduction of a guidewire 30 through a pre-formed apical puncture 32 in the left ventricle LV. A distal tip 34 of the guidewire 30 extends through the native aortic valve AV and into the ascending aorta AA. The distal tip 34 may extend further over the aortic arch, as seen in FIG. 2B, but the minimum extension is across the aortic valve AV.

FIG. 2B illustrates an introducer sheath 38 inserted into the LV through the apical puncture 32, with a balloon catheter 40 having a dilatation balloon 42 on a distal end passed over the guidewire 30 and through the sheath. As is known, prior to insertion of the sheath 38, a dilator having a gradually tapered tip (not shown) may first be inserted over the guidewire to enlarge the apical puncture 32. It should be noted at this point that the surgeon installs one or more purse-string sutures 44 in the tissue of the left ventricular apex surrounding the puncture 32. These sutures 44 are pre-implanted prior to formation of the initial puncture. In a preferred embodiment, the surgeon places a first line of purse-string sutures generally in a first circle in one direction, and then places a second line of purse-string sutures generally in a circle concentric to the first circle but in an opposite direction. The result is two concentric circles of separate purse-string sutures 44 defining a periphery within which the puncture is formed. The purse-string sutures 44 can therefore be pulled to cinch the ventricular tissue around whatever object passes through the puncture. In particular, the purse-string sutures 44 are tightened around both the guidewire 30 and introducer sheath 38. Installing the separate lines of purse-string sutures 44 in opposite directions helps prevent tearing of the ventricular tissue and provides a more uniform compression about whatever elongated object passes through the puncture.

As indicated in FIG. 2B, the dilatation balloon 42 expands radially outward into contact with the native aortic valve leaflets. With information concerning the size of the particular aortic valves, the balloon 42 is chosen so that it expands outward and nominally compresses the aortic valve leaflets against the surrounding aortic walls. There are various means for assessing the size of the particular patient's aortic valve, including ultrasound, which will not be described herein. Suffice it to say that following the valvuloplasty procedure seen in FIG. 2B, the native aortic valve leaflets are compressed outward against the aortic wall and a substantially circular orifice results. Additional details regarding pre-dilatation and valve replacement can be found in Applicant's U.S. Pat. No. 6,908,481 to Cribier, expressly incorporated by reference herein.

With reference now to FIGS. 3A-3E, a preferred method of deploying and implanting a prosthetic heart valve of the present invention using a transapical approach will now be described in more detail. The devices and methods disclosed herein are particularly well-suited for replacing a stenotic aortic valve, and as such that the pre-dilation procedure seen in FIGS. 2A-2B typically precedes the valve implantation so as to smooth out the contours of the annulus and leaflets. It should be noted, however, that the procedure described herein may be performed without valve pre-dilation.

Furthermore, the present procedure may be performed as a first time valve implant or to supplement a previous implant. A relatively large proportion of recipients of prosthetic heart valves are older, typically older than 60. Over time, prosthetic heart valves have been known to show reduced performance and even failure. Re-operating on septegenarians and even octogenarians is problematic. However, a port access procedure such as disclosed herein eliminates open-heart surgery and potentially cardiopulmonary bypass, and is therefore more desirable for the aging patient. Therefore, the present invention contemplates transapical implantation of a prosthetic heart valve over an existing prosthetic valve implant. In such a case, a pre-dilation step is typically not necessary, though it is conceivable.

Prior to a discussion of the procedure itself, it should be noted that a preferred delivery system of the present invention will be described in greater detail below with reference to FIGS. 4-13. The workings of the present delivery system may be more easily understood after an explanation of the steps taken to ultimately implant the valve in the aortic annulus.

The prosthetic heart valve implantation procedure described herein may be performed in conjunction with cardiopulmonary bypass, or without bypass in a so-called off-pump procedure. The necessity for bypass depends on a number of factors, including the patient's age, vulnerability to such a procedure, and viability of the native leaflets. Ideally, the implantation procedure is performed off-pump.

The surgeon or cardiologist first sizes the aortic valve using a physical sizer, or with echocardiography. The physician or operating room staff then crimps an expandable prosthetic valve 50 over the balloon 52 of a balloon catheter 54 (some of the elements presently described can be seen in the procedure drawings of FIGS. 3A-3E, while others can be seen in the system drawings of the FIGS. 4-13). The surgeon advances the balloon catheter 54 over a guidewire 60 (that might be the same guidewire 30 used in a pre-dilation procedure), through an introducer sheath 70 that has been inserted through the left ventricular apex puncture 32 with the help of a dilator 74 (sometimes also referred to as an introducer). The same purse-string sutures 44 that were used for the pre-dilation procedure may also be used to seal the ventricular tissue around the introducer sheath 70. In the absence of the pre-dilation procedure, the purse-string sutures 44 are pre-implanted prior to formation of the initial puncture. As before, the surgeon places a first line of purse-string sutures generally in a first circle in one direction, and then places a second line of purse-string sutures generally in a circle concentric to the first circle but in an opposite direction. The result is two concentric circles of separate purse-string sutures 44 defining a periphery within which the puncture is formed, and which seal around the introducer sheath 70.

Furthermore, the dilator 74 that expands the inner diameter of the puncture 32 and rides over the guidewire 60 may be inserted prior to or with the introducer sheath 70. Preferred dilator diameters range between 12 and 22 French. The introducer sheath 70 comprises the distal end of an introducer that will be described below. Introducer sheath diameters of no greater than 24 French, and desirably 22 or 24 Fr are preferred.

FIG. 3A shows the introducer sheath 70 passing into the left ventricle through the puncture 32 and over the guidewire 60 that extends upward through the calcified aortic valve AV. The surgeon locates a distal tip 72 of the introducer sheath 70 just to the inflow side of the aortic valve AV, as seen in FIG. 3A. At this point, it should be understood by those of skill in the art that the position of the introducer sheath 70 relative to the aortic valve AV, as well as the position of other elements of the system, is monitored using radiopaque markers and fluoroscopy, or using other imaging systems such as transesophageal echo, transthoracic echo, intravascular ultrasound imaging (IVUS), or an injectable dye that is radiopaque. A specific combination of such markers for the exemplary system will be described below.

FIG. 3B shows the advancement of the balloon catheter 54 over the guidewire 60 and through the introducer sheath 70. Ultimately, as seen in FIG. 3C, the prosthetic heart valve 50 is located at the aortic annulus and between the native aortic leaflets. FIG. 3C also illustrates retraction of the introducer sheath 70 from its more forward position in FIG. 3B to permit balloon inflation/valve expansion. Radiopaque markers may be provided on the distal tip 72 of the introducer sheath 70 to more accurately determine its position relative to the valve 50 and balloon 52.

Again, the precise positioning of the prosthetic heart valve 50 may be accomplished by locating radiopaque markers on its distal and proximal ends, or in-between, for example at a midpoint. Desirably, the surgeon can adjust the position of the valve 50 by actuating a steering or deflecting mechanism within the balloon catheter 54, as will be described below. Furthermore, the rotational orientation of the valve 50 can be adjusted relative to the cusps and commissures of the native aortic valve by twisting the balloon catheter 54 from its proximal end and observing specific markers on the valve (or balloon catheter) under fluoroscopy. One of the coronary ostia 80 opening into one of the sinuses of the ascending aorta is shown, and those of skill in the art will understand that it is important not to occlude the two coronary ostia with the prosthetic valve 50. It should also be noted that although the native leaflets of the aortic valve AV are shown coapting in FIG. 3A, and being flexibly displaced by the balloon catheter 54 in FIGS. 3B and 3C, they may actually be compressed further outward against the aortic annulus from a pre-dilation procedure.

Figure 3E:
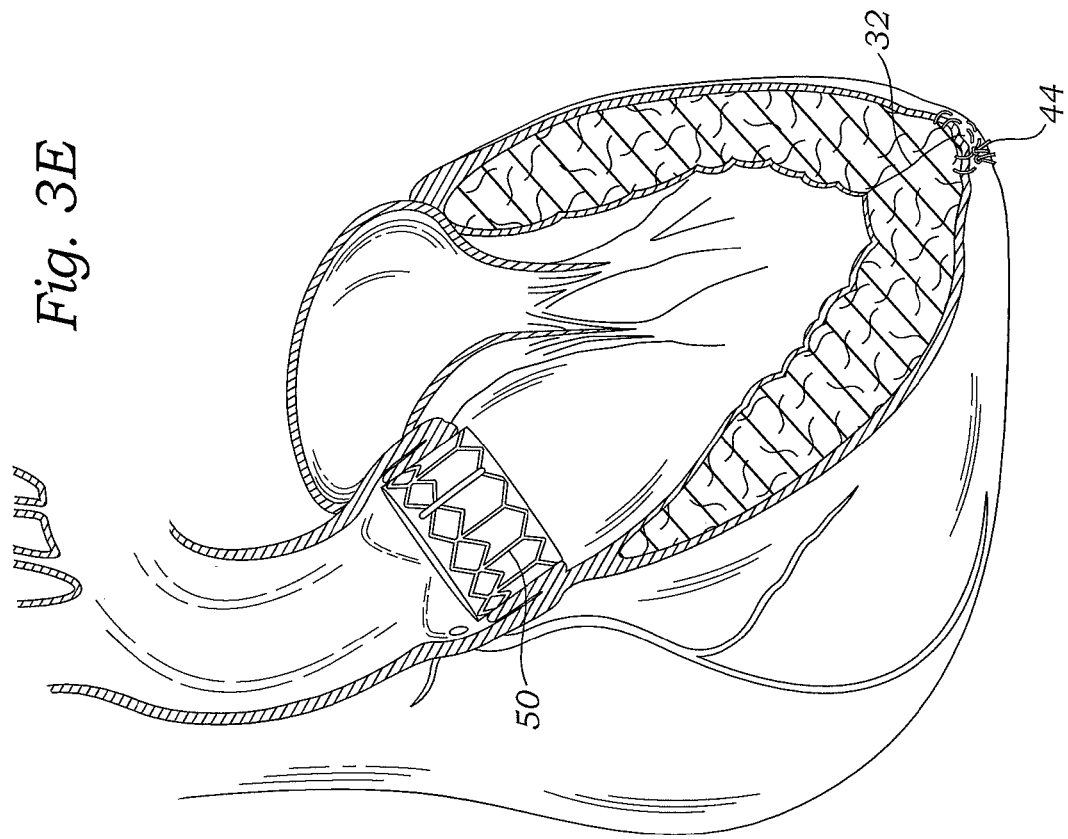
Figure 3D:
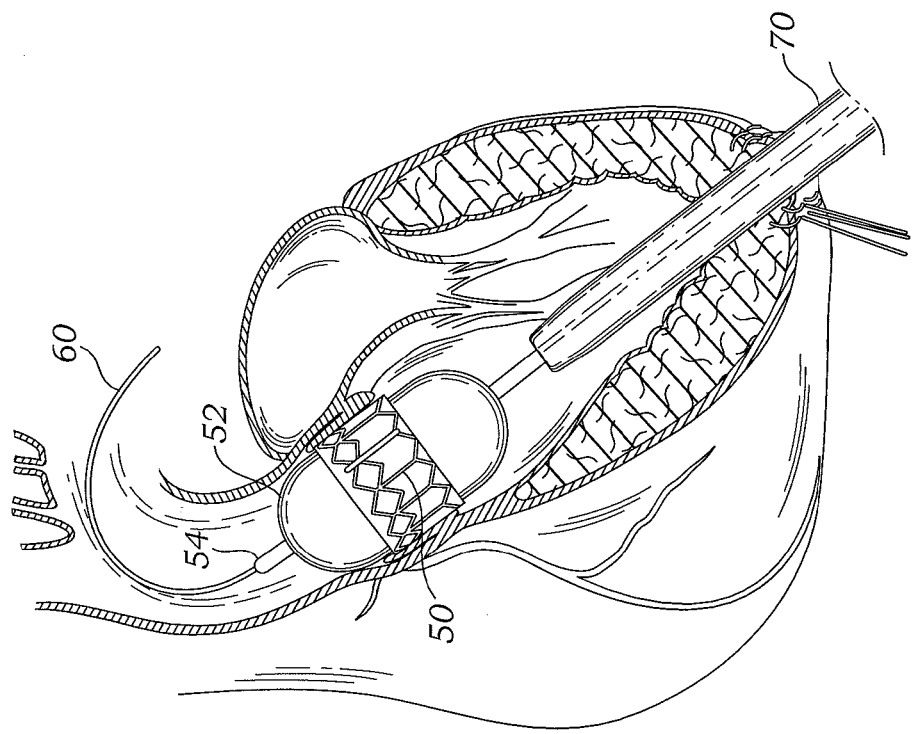

FIG. 3C shows the prosthetic heart valve 50 in its contracted or unexpanded state crimped around the balloon 52. When the surgeon is satisfied of the proper positioning and rotational orientation of the valve 50, the balloon 52 is expanded as seen in FIG. 3D. Proper size measurement of the native aortic valve AV enables the surgeon to select an optimum-sized valve 50 such that it expands outward into good contact with the aortic annulus. The term "good contact" implies sufficient contact to ensure that the prosthetic heart valve 50 does not migrate after implant. Excessive expansion of the valve, however, may damage surrounding tissue or interfere with the performance of adjacent valves.

A number of devices are available to assist in anchoring the prosthetic valve 50 into the aortic annulus, such as barbs and the like. A preferred configuration of prosthetic heart valve 50 for use with the present invention is disclosed in co-pending U.S. patent application Ser. No. 12/480,603 to Hariton, filed Jun. 8, 2009, which disclosure is expressly incorporated herein by reference. Another valve is disclosed in U.S. Pat. No. 7,276,078 to Spenser, filed Jun. 30, 2004, which disclosure is also expressly incorporated herein by reference. Of course, the valve 50 can take a variety of different forms but generally comprises an expandable stent portion that supports a valve structure. The stent portion has sufficient radial strength to hold the valve at the treatment site and resist recoil of the stenotic valve leaflets. Additional details regarding preferred balloon expandable valve embodiments can be found in U.S. Pat. Nos. 6,730,118 and 6,893,460, both to Spenser and both of which are expressly incorporated herein by reference. The preferred prosthetic heart valve 50 includes sufficient irregularity on its outer surface such that it may be anchored in the aortic annulus without the use of barbs or other tissue piercing structure.

Once the valve 50 is properly implanted, as seen in FIG. 3D, the surgeon deflates the balloon 52, and withdraws the entire delivery system including the balloon catheter 54 over the guidewire 60. The introducer sheath 70 is then withdrawn, followed by the guidewire 60. Ultimately, the purse-string sutures 44 previously described are cinched tight and tied to close the puncture 32, as seen in FIG. 3E.

It is important to recognize that the heart valve delivery system of the present invention is particularly well-suited for the antegrade, left ventricular apex, "transapical," approach. More particularly, the mini-thoracotomy approach requires relatively short instruments. Therefore, the portion of the introducer sheath 70 that extends into the body is desirably no more than about 8 inches (20 cm) long, and the length of the balloon catheter 54 that may extend into the introducer sheath 70, i.e., the "working length," is desirably no more than about 24 inches (61 cm). Further specifics on the relatively short length of the balloon catheter 54 and introducer sheath 70 will be provided below. The short length of the prosthetic heart valve delivery system described herein is also well-suited for other anatomical approaches, including through the carotid or subclavian arteries. The short length of the system is desirable because it enhances controllability and steerability of the distal end, relative to longer systems, which helps improve accuracy and reduced time for valve positioning.

The delivery system of the present invention essentially comprises an introducer 100, the balloon catheter 54, and attendant couplers and operating structures, including a loader 140 between the introducer and balloon catheter as seen in FIG. 7. The introducer 100 is illustrated in FIGS. 4-6, while the balloon catheter 54 and loader 140 are shown in FIGS. 7-12. It should be noted that the delivery system is similar to another system used to percutaneously implant a prosthetic aortic valve, which is disclosed in co-pending U.S. Patent Publication No. 2007-0005131 to Taylor, filed Jun. 13, 2005, and expressly incorporated herein by reference. The present system differs in several aspects that make it more suitable for a transapical, port-access, or direct-access approach, although some features are common.

As seen in FIGS. 4 and 4A, the introducer 100 comprises the aforementioned distal sheath 70 coupled to an introducer housing 102 containing a series of valves. The exploded views of FIGS. 5A and 5B shows an end cap 104 detached from the introducer housing 102. The end cap 104 includes a flanged nipple 105 for mating with the loader 140, as will be explained below. The end cap 104 threads or otherwise attaches to the housing 102 and retains therein, in series from proximal to distal, a cross-slit valve 106, a disk valve 108, a spacer 110, and a duck-bill valve 112. These three valves function to provide a seal when no instruments pass through the introducer 100, and when several different sizes of instruments pass therethrough. For example, the valves seal around both the guidewire 60 and the balloon catheter 54 as previously shown. The introducer sheath 70 extends into the body vessel, with the introducer housing 102 located outside the body vessel. In a preferred embodiment, the introducer sheath 70 possesses an external hydrophilic coating and has a length of between about 20-24 cm so that it may extend through the access incision 20 (see FIG. 1), into the left ventricle and reach the aortic annulus.

As seen best in FIGS. 5 and 5A, the introducer sheath 70 attaches to the housing 102 via a sealing extension 122 that mates with a distal nipple 124 extending from the housing 102. Preferably adhesive is used between these two mating sections. A threaded nut 126 rides over the sheath 70 and couples to threading 128 provided on the housing 102 just proximal to the nipple 124. In this way, the various components can be manufactured (typically molded or extruded) separately and easily coupled together during assembly. Adhesive may be applied to the threading 128 prior to coupling the nut 126 for a more secure final assembly.

A side port tube 130 extends at an angle away from the introducer housing 102 and terminates in a three-way stopcock 132. This permits the user to infuse medicaments or other fluids through the lumen of the introducer 100 even if devices such as the balloon catheter 54 are present therein.

FIGS. 6A-6D show further details of the introducer 100, including a series of depth markings 133 on a distal section of the sheath 70. The markings 133 indicate the distance in millimeters from the distal tip 72 so that the depth to which the distal tip extends into the left ventricular apex can be easily seen.

FIGS. 6B and 6C illustrate an advantageous construction in which the sheath 70 has greater flexibility along a distal section than along a proximal section. Specifically, the sheath 70 includes a distal section 134 having a length l that is more flexible than a proximal section 135, wherein the free length of the sheath 70 is L (extending from the threaded nut 126). FIG. 6C shows the internal construction of the sheath 70, which includes an inner tubular liner 136, a reinforcing coil 137, a distal exterior tube 138 and a proximal exterior tube 139. The liner 136 and coil 137 extend the free length L of the sheath 70, while the exterior tubes 138, 139 abut in series. The stiffness of the proximal exterior tube 139 is desirably greater than that of the distal exterior tube 138 to provide the differing flexibilities. Although two discrete sections each with constant stiffness are shown, the flexibility may be varied in more than two sections, and more gradually, with similar results.

By providing a more flexible distal section 134, movement of the heart muscle surrounding the introducer sheath 70 (such as in the position of FIG. 3D) is accommodated with less trauma to the heart tissue. That is, the preferred procedure is with a beating heart with the left ventricle continually contracting and relaxing, which creates a significant amount of tissue/introducer movement. Permitting the distal end of the introducer to flex, or be floppy, helps reduce damage to the heart wall. Moreover, the surgeon often manipulates the catheter or introducer for better implant site access, which with a stiffer sheath may cause trauma to the heart wall. At the same time, the stiffer proximal section 135 ensures that the introducer 100 projects out from the operating field in a relatively straight line, with minimal floppiness, which is desired by surgeons. Sometimes a stabilizer at the point of incision may be used, which reduces the heart wall movement, though the floppy distal end of the sheath still provides a benefit.

The liner 136 provides a smooth inner surface through which the balloon catheter with heart valve may pass without hindrance, and the coil 137 provides hoop strength to the tubular structure to prevent kinking. The sheath 70 may be fabricated using a number of tube forming techniques, such as extrusion.

In one embodiment, the free length L of the sheath 70 is between about 20-24 cm, while the distal section 134 has a length l of between about 4 cm and one half the free length L. More preferably the distal section 134 has a length l of between about 6-9 cm, and most preferably about 9 cm. The length l should be sufficient to permit the floppy portion of the sheath 70 to extend at least 4 cm into the heart wall.

In an exemplary embodiment, the inner liner 136 and exterior tubes 138, 139 are formed of the same material for better melding, while the coil 137 is metallic. One particular combination is the liner 136 and exterior tubes 138, 139 made of a nylon block copolymer sold under the tradename PEBAX®, while the coil 137 is stainless steel. The commercial PEBAX polymers consist of polyether blocks separated by polyamide blocks. The polyether blocks may be based upon polyethylene glycol, polypropylene glycol, or polytetramethylene ether glycol. The polyamides are usually based upon nylon-11 but may be based upon nylons 6 of nylon-6,6 or even a copolymer such as nylon-6/nylon-11. The polymers range in hardness as measured in durometer from Shore A 60 to Shore D72, and the proximal exterior tube 139 has a greater durometer than the distal exterior tube 138. A selection of PEBAX compositions and their respective physical properties are provided on the website, www.pebax.com, in particular under the link, "Medical Applications." PEBAX® is a registered trademark of Arkema Inc. of Paris, France, with U.S. Corporate offices in Philadelphia, Pa.

FIG. 6D also shows an advantageous visualization system for the distal tip 72 of the introducer sheath 70. A circular array of marker dots 73 at the distal tip 72 can be seen under fluoroscopy, and in clear contrast to marker bands provided on the balloon catheter 54, as explained below.

FIG. 7 illustrates in perspective the balloon catheter 54, which comprises an assembly of interrelated components commencing on a proximal end with a luer fitting 142 and terminating at a distal end in a soft tip 144. The balloon catheter 54, also shown in plan, sectional, and exploded views in FIGS. 8-12, comprises a control handle 150 having the luer fitting 142, a balloon inflation connector 152, a deflection actuator 154, and a pusher actuator 156. A pusher body 158 extends from the handle 150 around a balloon deflection tube 160 having the expandable balloon 52 located just proximal to the soft tip 144. FIG. 7 illustrates a balloon sheath 161 covering the balloon 52 which protects the balloon during shipping and is removed prior to use of the system. An elongated stationary protective sleeve 162 also extends from the handle 150 over a majority of the pusher body 158 and forms an exterior surface of the balloon catheter 54 along much of its length. The loader 140 shown in perspective in FIG. 7A will be described in more detail below and provides a coupling between the balloon catheter 54 and the above-described introducer 100.

As mentioned, the present application discloses an advantageous visualization system for the distal tip 72 of the introducer sheath 70. Specifically, at least one marker band will be provided on the proximal end of the balloon 52, and also on a distal end of the pusher body 158. The axial proximity of the distal end of the pusher body 158 and the proximal end of the balloon 52 can therefore be easily seen to facilitate their engagement. In addition, the circular array of marker dots 73 at the distal tip 72 of the introducer sheath 70 clearly contrasts with the marker bands on the balloon catheter 54 and the pusher body 158, and helps the surgeon ensure that the introducer has been retracted far enough at the time of valve positioning and balloon expansion.

Prior to a detailed description of the exemplary balloon catheter 54, its interaction with the introducer 100 via the loader 140 will be explained. As seen in FIG. 7A, the loader 140 has a generally tubular body 172 and a slightly externally tapered distal nose 174 that fits within the introducer 100, and specifically through the series of valves 106, 110, 112 shown in FIG. 6B. The loader body 172 includes a pair of attached cantilevered fingers 176 extending longitudinally with internally facing snap ridges for securing the loader 140 to a nipple on the proximal end cap 104 of the introducer 100. The loader 140 facilitates introduction of the balloon catheter 54 into the introducer 100. As described above, the introducer housing 102 contains the series of valves 106, 110, 112 that in aggregate provide an effective fluid seal against egress of blood through the introducer 100 in the presence or absence of different sized medical implements. The distal nose 174 of the loader 140 extends through the introducer housing 102 and through these valves 106, 110, 112 (see FIG. 14A) to hold them open and provide a smooth internal lumen which matches the size of the lumen of the introducer sheath 70. In this way, the somewhat irregular contours of the balloon catheter 54 having a prosthetic valve 50 crimped around the balloon 52 may smoothly pass into the introducer sheath 70.

A loader seal, seen exploded in FIG. 7A, positioned within a proximal housing 178 comprises a pair of annular washers 180 and a resilient vent member 182. As seen in FIG. 7, the protective sleeve 162 passes through the loader 140, and the loader seal prevents fluid from escaping around the sleeve. The vent member 182 includes a pair of lateral buttons 184 that project through apertures in the side of the proximal housing 178. Inward depression of one or both buttons 184 causes deformation of the vent member 182, which in turn opens the distal space within the loader body 172 to the atmosphere. Any air entrained in the blood within the loader body 172 can thus easily be vented with one hand. The one-handed aspiration is both more convenient and also helps avoid inadvertent misalignment of the heart valve from unscrewing a valve cap to vent, a two-handed operation, which is the conventional arrangement. Moreover, eliminating the previous threaded cap arrangement for tightening a resilient seal with the passive loader seal means that movement of the protective sleeve 162 (and delivery catheter 54) is never prevented by the loader valve. In this way, movement of the catheter 54 is decoupled from the loader 140 and attached introducer 100.

Prior to balloon expansion as seen in FIG. 12, the loader 140 couples over the distal extent of the balloon catheter 54, as seen in FIG. 7. The distal nose 174 inserts into the introducer housing 102 and the cantilevered loader fingers 176 mate with the flanged nipple of the end cap 104 (FIG. 14A). The balloon catheter 54 is thus coupled to the introducer 100. Sliding the entire balloon catheter 54 distally permits the irregular contours of the distal extremity thereof to pass safely across the valves 106, 110, 112 and into the introducer sheath 70. The loader 140 remains coupled to the introducer 100 during the valve implant procedure, and the vent member 182 can be actuated as needed to ensure no air remains in the system.

The various components of the balloon catheter 54 will now be described with respect to FIGS. 8-12. The catheter 54 includes the proximal control handle 54 and a plurality of concentric tubes that extend distally to the soft tip 144. In the exemplary embodiment, five concentric tubes of gradually smaller size connect to or extend into the handle 150, as seen in FIG. 10B. The handle 150 includes two molded halves having a plurality of inner walls and cavities to contain the various components.

Figure 9:
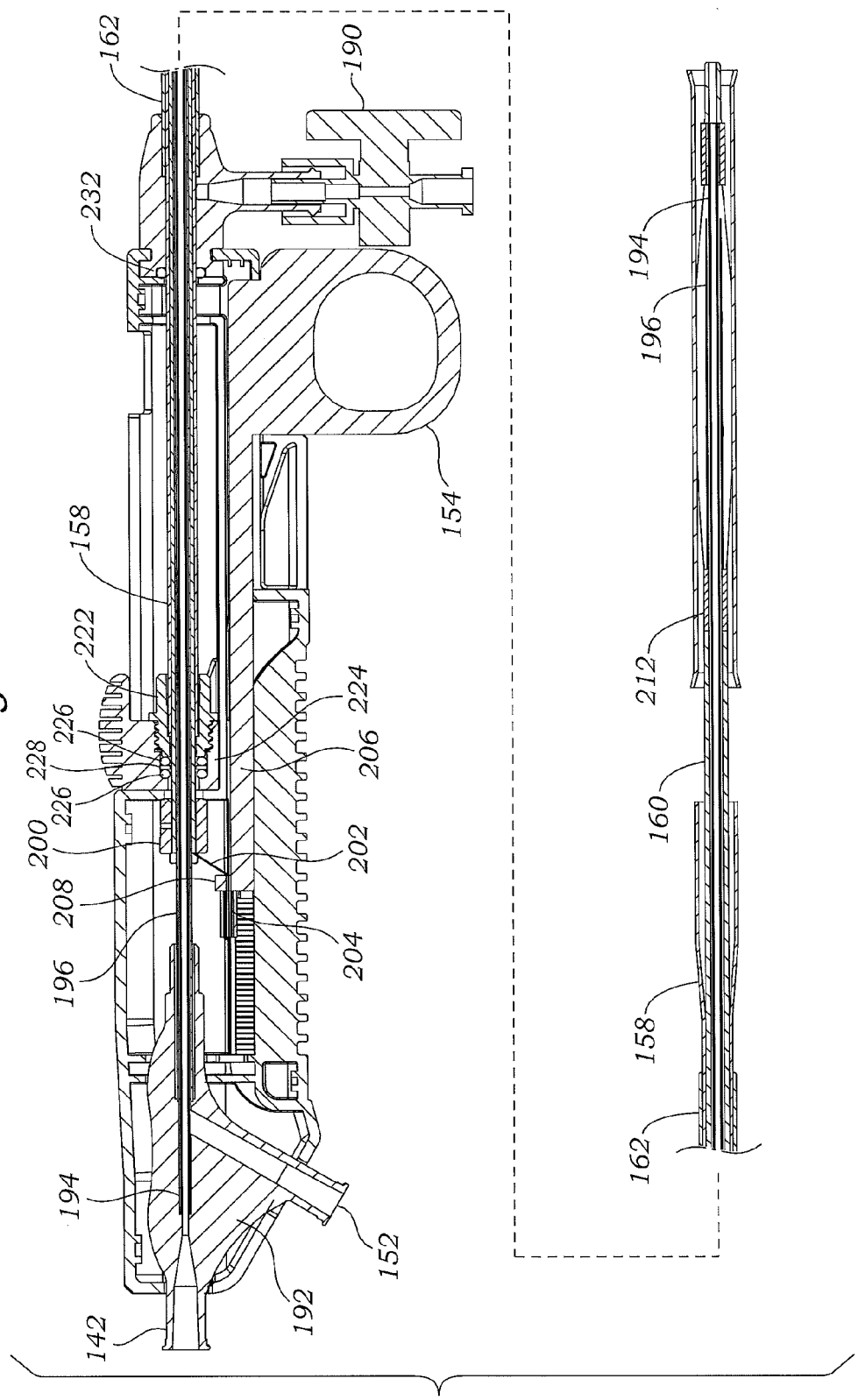
FIG. 9 is a longitudinal sectional view of a proximal control handle of the balloon catheter of FIG. 7.

The handle 150 includes a number of control components and is shown in section in FIG. 9 and exploded in FIGS. 10A and 10B. Specifically, the deflection actuator 154 in the form of a trigger controls deflection of the distal tip of the balloon deflection tube 160, the pusher actuator 156 in the form of a slider controls longitudinal movement of the pusher body 158, and operation of a stopcock 190 permits infusion of fluids to flush a space between the introducer sheath 70 and the pusher body 158. Furthermore, a Y-port 192 at the proximal end of the handle 150 provides a longitudinal passage leading to the luer fitting 142 and an angled passage leading to the balloon inflation connector 152. An inner tube 194 (smallest) having a throughbore extends the length of the balloon catheter 54 from the luer fitting 142 through the distal soft tip 144 (see FIG. 12). The inner tube 194 provides a channel for passage of a guidewire, such as shown at 60 in FIG. 3D. The luer fitting 142 also may provide an entry point for injection of radiographic contrast medium though the inner tube 194, which is useful to check for perivalvular leaks after the prosthetic valve is implanted.

Still with reference to FIGS. 8-10, and in particular FIG. 9, a balloon inflation tube 196 (second smallest) surrounds the inner tube 194, extending from the Y-port 192 in a distal direction and terminating within the balloon 52. As seen in FIG. 9, the Y-port 192 includes a stepped longitudinal bore having a larger distal portion that sealingly receives the balloon inflation tube 196, and a smaller middle portion that sealingly receives the inner tube 194. The angled passage leading to the balloon inflation connector 152 fluidly communicates with a space outside of the inner tube 194 that opens to the lumen of the balloon inflation tube 196. With this configuration, fluid injected into the balloon inflation connector 152 passes into and travels the length of the balloon inflation tube 196 until it exits from the open distal end 198 thereof, within the balloon 52 (as seen in FIG. 12). Additional fluid egress ports (not shown) may be provided in the balloon inflation tube 196 along the length of the balloon 52 for even inflation, and in particular ports proximal and distal to the prosthetic heart valve 50 are beneficial to help expand both ends of the valve at the same rate.

The balloon inflation tube 196 extends through the lumen of the balloon deflection tube 160 (third smallest) which has a proximal end anchored by a collar 200 fixed within a cavity of the handle 150. The balloon deflection tube 160 has a particular construction that enables flexing along its length without kinking, and has a deflectable distal tip. More particularly, the balloon deflection tube 160 desirably includes a braided tube along its length to prevent kinking, a coil structure at its distal tip for deflection, and a deflection wire 202 that extends from the proximal end to the coil.

The deflection wire 202 also includes a plug 204 fixed on its proximal end acted on by a rail 206 that slides longitudinally within the handle 150. Specifically, the deflection wire 202 passes through an aperture of a finger 208 on the rail 206, which aperture is smaller than the plug 204. The plug 204 is desirably cylindrical and may be constrained within a small guide sleeve 210 held within a cavity of the handle 150. The rail 206 forms part of a trigger assembly and moves with the trigger 154. Pulling the trigger 154 to the left from its position in FIGS. 8 and 9 will displace the plug 204 to the left, also pulling the deflection wire 202 to the left, or in a proximal direction. The deflection wire 202 in turn attaches to one side of the coil at a distal tip 212 of the balloon deflection tube 160, and pulling on the wire thus deflects the distal tip, as seen in FIGS. 14D and 14E. Of course by rotating the entire balloon catheter 54 about its axis the deflecting segment 212 may be steered in any direction. The coil provides both flexibility and resiliency such that release of tension on the deflection wire 202 permits the deflecting segment 212 to return to a straight orientation.

The construction of the deflection tube 160 enables a size reduction from prior designs that ultimately enables a size reduction of the valve 50 and balloon 52. In one embodiment, the deflection tube 160 has a dimension no greater than 8 French. The braided proximal portion provides flexibility and column strength, while the distal coil enables the deflection only at the distal end. The distal tip 212 having the coil structure desirably has a length of about 4 cm. This construction also facilitates manufacture, as the braided proximal portion and coil with attached deflection wire 202 are easily combined using welding or the like.

The second largest tube is the pusher body 158, which is tubular until an outwardly flared sleeve 220 on its distal end (see FIGS. 8 and 11). A proximal end of the pusher body 158 affixes to a threaded sleeve 222 that couples with an internally threaded bore of a slider cap 224, as seen in FIGS. 9 and 10B. One or more passive O-ring seals 226 within the bore of the slider cap 224 permit relative movement of the slider member over the balloon deflection tube 160 while sealing against blood leakage therebetween. Desirably, two O-rings 226 sandwich an annular polymer (e.g., nylon) washer 228 to help even out the forces on each of the O-rings and therefore enhance the quality of the fluid seal around the balloon deflection tube 160. Translation of the slider 156 and attached slider cap 224 along a corresponding longitudinal slot in the handle 150 thus displaces the pusher body 158 relative to the handle and to the balloon deflection tube 160. Previous devices included separate handles and the seal would be positioned within a threaded cap that required tightening. The passive nature of the O-ring seal eliminates the two-handed tightening operation and also avoids any misalignment of the heart valve 50 once positioned from inadvertent movement of the balloon deflection tube 160.

Moreover, the design of the handle 150 facilitates one-handed operation of the two primary movements of the balloon catheter 54—deflection of the distal tip and linear movement of the pusher body 58. The handle 150 preferably includes ergonomic ribs 230 on its underside, as seen in FIG. 8, which, coupled with ribs on the slider 156 assist in moving the pusher body 158 along the catheter.

The pusher body 158 slides over the balloon deflection tube 160 as well as inside of the stationary protective sleeve 162 (the largest tube). As seen in FIG. 9, the sleeve 162 affixes into a stepped bore of a housing of the stopcock 190, which in turn attaches to a distal end of the handle. An O-ring seal 232 held within the stopcock housing (or between the housing and the handle 150) contacts and seals against the exterior of the moving pusher body 158 and prevents leakage of fluid from the concentric space between the pusher body 158 and the stationary protective sleeve 162. Saline or other such fluid may thus be infused in through the stopcock 190 to travel down and flush the concentric space between the pusher body 158 and the stationary protective sleeve 162.

FIG. 11 is an elevational view of the distal end of the balloon catheter 54 showing the balloon 52 deflated and its proximal end spaced from the pusher sleeve 220, while FIG. 12 shows the distal end of the balloon catheter 54 with the balloon 52 inflated.

The inner tube 194 passes through the balloon 52 and terminates at a distal end that is capped by the aforementioned soft tip 144. The soft tip 144 facilitates introduction of the balloon catheter 54 and reduces trauma to surrounding tissue. This is particularly important in the preferred procedure of the present invention where the catheter enters the apex of the left ventricle and travels through the aortic valve into the ascending aorta. As was seen in FIG. 3D, the distal tip of the catheter may extend far enough to enter the aortic arch, and the soft tip 144 thus prevents rupture or other abrasion to the surrounding vascular tissue. FIG. 13 also illustrates the open distal end of the inner tube 194 and soft tip 144 through which first a guidewire 62 may be passed and then radiographic contrast medium may be injected to test valve sufficiency after implant.

The balloon 52 includes a first cone portion 240, a main cylindrical portion 242, and a second cone portion 244. The prosthetic heart valve 50 desirably crimps around the main cylindrical portion 242 for even cylindrical expansion, such as shown in phantom in FIG. 12. The balloon 52 can be formed of nylon, and is rated at a burst pressure of 6-8 atm. In preferred embodiments, the expanded diameter of the balloon ranges from about 20 to 28 mm, the particular size depending on the size of the heart valve 50 being implanted.

Figure 15:
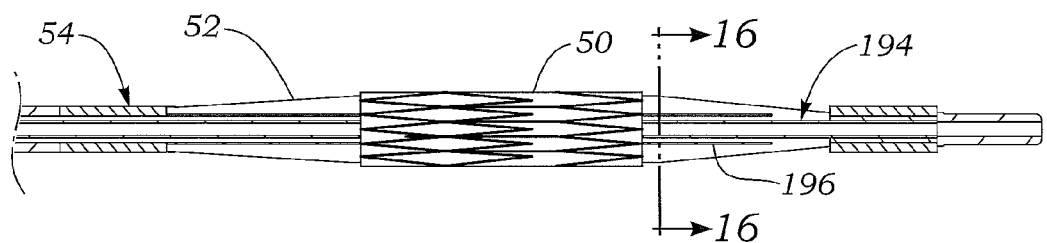
FIG. 15 is a longitudinal sectional view of a distal end of an exemplary balloon catheter showing a prosthetic heart valve crimped over a balloon folded in a way that enhances visualization of the valve during implant.

FIG. 15 is a longitudinal sectional view of a distal end of the exemplary balloon catheter 54 showing a prosthetic heart valve 50 crimped over the balloon 52. The heart valve 50 has a shorter length than the balloon 52 leaving proximal and distal exposed portions thereof.

The balloon 52 is folded in a way that enhances visualization of the valve during implant. Specifically, certain conventional folding techniques resulted in wrinkling of the balloon 52. For example, a common way to fold a catheter balloon is to first form a trifold and then wrapping the leaves of the trifold around the balloon catheter axis. Folding techniques like this often leave wrinkles or ripples even if done carefully. Such irregularities show up on echocardiography, which can interfere with precise location of the proximal and distal ends of the valve 50 relative to the implant site. The balloon 52 of the present invention on the other hand is folded in a manner that reduces if not eliminates irregularities that show up on echocardiography, thus enhancing the ability to properly locate the heart valve 50 at the aortic annulus.

Figure 16:
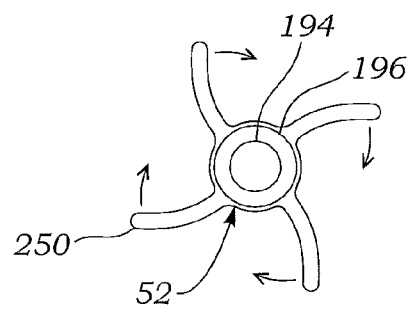
FIG. 16 is a radial section of the folded balloon of FIG. 15.
Figure 17:
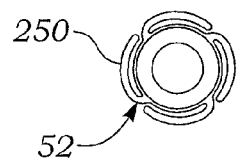
FIG. 17 is a radial section of the balloon of FIG. 16 illustrating a preferred folding technique.

FIG. 16 is a radial section of the folded balloon of FIG. 15, and shows four leaves 250 of the balloon 52 folding in a clockwise manner around the inner tubes 194, 196, though of course the direction that the leaves are wrapped is not critical. FIG. 17 illustrates the leaves 250 prior to folding. The leaves 250 extend longitudinally along the balloon 52 and comprise even circumferential spans of the balloon 52. By careful selection of the radial dimension of each leaf 250, the resulting wrapped structure in FIG. 16 is minimized for that size of balloon, and ensuring even circumferential wrapping rates results in longitudinal lines in the wrapped structure. The longitudinal fold lines contrast under fluoroscopy with the radial ends of the valve 50, thus ensuring a clear view of the valve. Moreover, the longitudinal fold lines contrast with marker bands on the balloon and the pusher, as explained above. There may be four or more, possibly 6-8 folds or pleats pre-formed in the balloon which also facilitate deflation and removal through the valve and introducer.

In use, the present invention provides a novel and effective way for implanting a prosthetic heart valve 50 in the aortic annulus. The steps of the procedure have been described above with respect to FIGS. 1-3, at least as far as the final implantation steps. A description of the advantageous use of the exemplary balloon catheter 54 and introducer 100 in performing the entire procedure will now be provided with reference to FIGS. 13 and 14A-14E, which are in situ views of the system without the valve 50.

First, as mentioned above, the physician determines the size of the patient's annulus. This can be done physically by creating the incision 20 and puncture 32 (FIGS. 1 and 2A) in the left ventricular apex, and inserting a sizing tool into the aortic annulus. However, the puncture 32 may not be large enough to pass a conventional sizer, and an alternative technique such as echocardiography or other such imaging system may be utilized.

Next, the balloon catheter 54, introducer 100, loader 140, and prosthetic heart valve 50 are selected, and prepared for use by removing them from any packaging and rinsing or sterilizing as needed. A pre-dilation step as described above with respect to FIGS. 2A-2B may be performed to enlarge or crack existing calcification in the aortic annulus.

The process of crimping the prosthetic heart valve 50 over the balloon 52 may be accomplished in a number of ways, and there are suitable devices on the market for crimping balloon-expanding stents over balloons. In a preferred embodiment, a device having a compressing mechanism that works like the aperture iris of a camera is utilized. In such a device, multiple continuous segments around the periphery of the prosthetic heart valve 50 close separately but in concert so that uniform inward pressure is exerted on the heart valve. The devices typically operate manually.

Subsequently, the aforementioned pusher body 158 and flared sleeve 220 are advanced distally over the proximal end of the balloon 52, as seen in FIG. 13. The loader 140 is then secured over the distal end of the balloon catheter 54, including the assembly of the balloon 52 and prosthetic valve (not shown).

At this point, or at the same time as balloon catheter preparation, the introducer 100 is positioned within the left ventricle as seen in FIG. 3A. Again, the purse-string sutures 44 maintain a fluid tight seal around the introducer sheath 70. During the entire procedure the heart may continue beating. The physician inserts the distal nose 174 of the loader 140 into the proximal end cap 104 of the introducer 100 and bottoms the loader out such that the cantilevered fingers 176 engage the flanged nipple 105 of the introducer, as seen in FIG. 14A. At this point, the balloon catheter 54 is ready for introduction in the body.

The pusher body 158 and pusher sleeve 220, as well as the stationary protective sleeve 162, facilitate advancement of the deflecting segment 212 and attached balloon 52 having the valve 50 crimped thereon through the introducer sheath 70 and its valves 106, 110, 112. In particular, the flared pusher sleeve 220 surrounds the deflecting segment 212 and a proximal portion of the balloon 52 during passage through the introducer sheath 70. The pusher sleeve 220 secures the crimped valve from movement relative to the balloon 52. Eventually, proximal retraction of the pusher body 158 relative to the balloon deflection tube 160 frees the deflecting segment 212 for angled movement, and the balloon 52 for expansion.

Figure 14B:
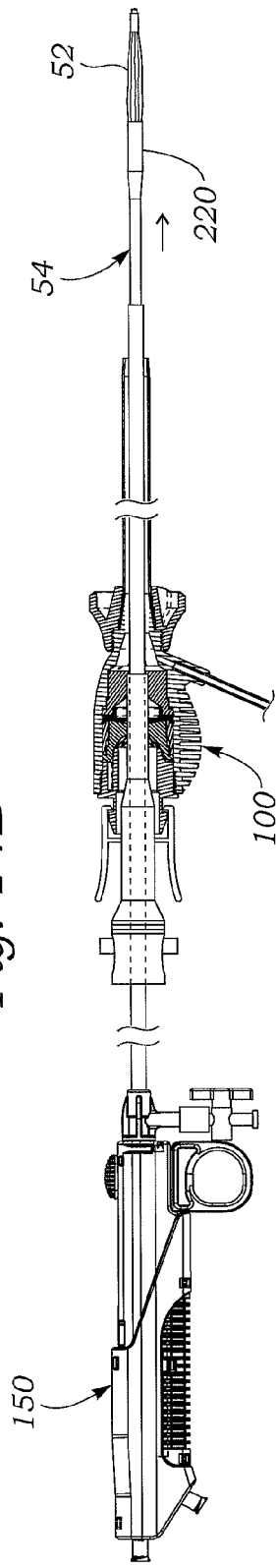
FIGS. 14B-14E are views similar to FIG. 14A showing use of the heart valve delivery system disclosed herein in situ at the occurrence of a series of steps in a valve implant procedure.

The physician then distally advances the balloon catheter 54 with respect to the loader 140 and introducer 100 into a position such as that shown in FIG. 14B. In this state, the balloon 52 with valve may be advanced to its eventual implant position using echocardiography, for example.

Figure 14C:
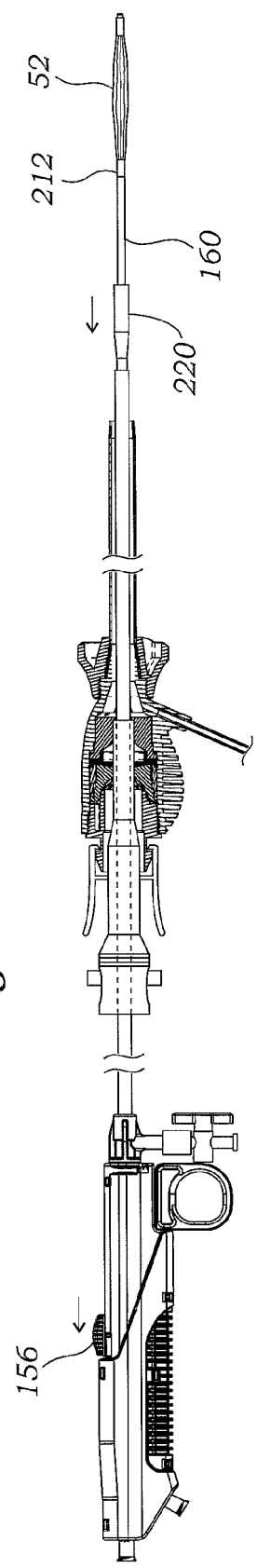
Figure 14D:
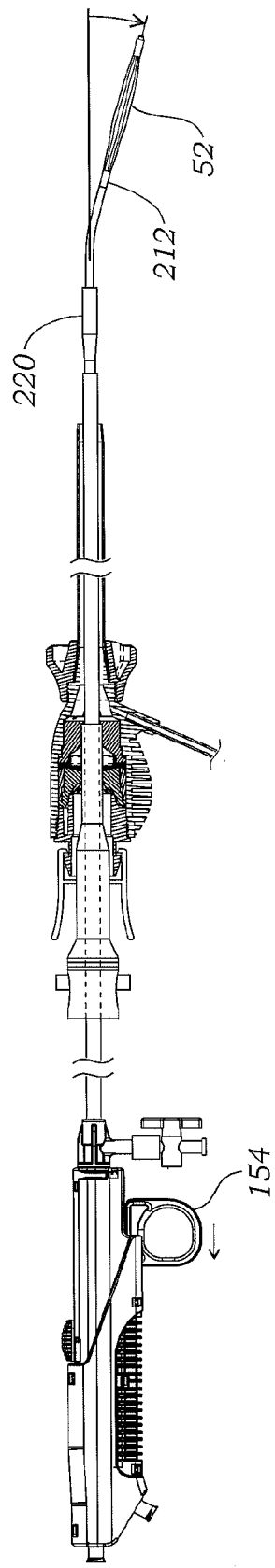
Figure 14E:
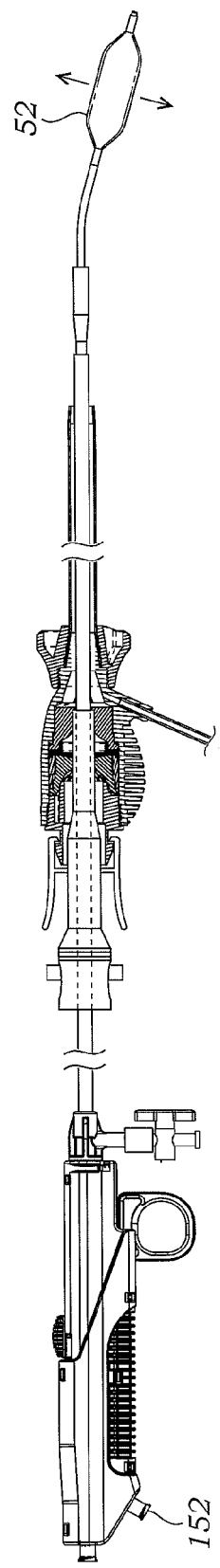

The physician then retracts the pusher sleeve 220 from the deflecting segment 212 and the proximal portion of the balloon 52, as seen in FIG. 14C, by simply sliding back the pusher actuator 156 on the handle 150. The stationary protective sleeve 162 around the pusher body 158 serves to decouple movement of the pusher from the valves of the introducer, thus reducing friction on the pusher. Also, the one-handed operation of sliding back the pusher actuator 156 while grasping the handle 150 greatly reduces the chance of misalignment of the valve position.

The physician may further advance and angle the balloon 52 until it reaches the position shown in FIG. 3C. The entire operation is visualized using radiographic markers and fluoroscopy, and the precise positioning of the balloon 52 and prosthetic valve 50 mounted thereon is accomplished by axial movement and rotation of the catheter 54 coupled with angular changes of the deflecting segment 212, as seen in FIG. 14D. Specifically, as the prosthetic valve 54 advances it is aligned as much as possible along the flow axis of the native aortic valve AV by gross movement of the catheter 54 and slight changes in its angular orientation by tensioning the deflecting wire 202 with the deflection actuator 154.

As mentioned above, the deflection wire 202 (FIG. 10B) extends from the handle 150 along the balloon deflection tube 160 and terminates at the deflecting segment 212, and preferably at a distal end of a coil spring therein (not shown). Pulling the deflection wire 202 causes the deflecting segment 212 to be pulled to the side of attachment of the wire, thus deflecting the distal end of the catheter and balloon 52, as in FIG. 14D.

Ultimately, the valve 50 is positioned correctly as in FIG. 3C taking care that the valve 50 is not liable to block either of the coronary ostia 80 when expanded. Saline mixed with contrast is then injected through the balloon inflation connector 152 which passes through the length of the balloon inflation tube 196 to fill the balloon 52, as seen in FIG. 14E. The balloon 52 is of a type that has a maximum expanded diameter which has previously been selected to properly expand the prosthetic heart valve 52 to its optimum diameter in contact with the surrounding aortic valve AV, and calcified leaflets if they remain in place. The step is illustrated in FIG. 3D. The balloon 52 expands the prosthetic heart valve 50 to implant it in the annulus, after which the balloon is deflated and removed from within the valve.

Subsequently, radiographic contrast medium may be injected from the proximal luer connection 142 of the balloon catheter 54 to egress through the distal soft tip 144 and test the efficacy of the just-implanted prosthetic valve 50. If the valve is properly functioning, the balloon catheter 54 is withdrawn into the introducer sheath 70, which is removed from the puncture 32. The purse-string sutures 44 are closed up to seal the puncture 32.

Once again, the delivery system described herein is particularly well-suited for an antegrade, transapical approach, partly because of its relatively short length. With reference to FIG. 4A, the entire length of the introducer 100 is approximately 13 inches (33 cm), while the length of the sheath 70 that may extend within the body is between about 20-24 cm. The portion of the balloon catheter 54 that extends into the introducer 100 (that is, the portion of the balloon catheter from the distal soft tip 144 to approximately the deflection handle 154) is preferably no more than about 24 inches (61 cm), which permits about 11 inches (28 cm) of the balloon catheter to extend beyond the introducer distal tip 72 (see FIG. 4). It should be noted that the relatively short length of the delivery system is unsuited for a longer, more circuitous approach through the peripheral vasculature, such as shown in co-pending U.S. Patent Publication No. 2007-0005131 to Taylor. Also, the steering mechanism is provided on the balloon catheter 54 itself, rather than on a secondary catheter used for guiding the balloon catheter, as is done in U.S. Patent Publication No. 2007-0005131. The short length of the balloon catheter and the ability to directly manipulate it greatly enhances successful positioning of the prosthetic heart in the aortic annulus.

While the invention has been described in its preferred embodiments, it is to be understood that the words which have been used are words of description and not of limitation. Therefore, changes may be made within the appended claims without departing from the true scope of the invention.

What is claimed is:

1. A method of deploying and implanting a prosthetic heart valve into a beating heart, comprising:
   while the heart is beating, forming an incision and passing an introducer having a stiff proximal section into the left side of the heart;
   advancing a balloon catheter having a heart valve mounted on a distal balloon into and through the introducer such that the heart valve is positioned within the aortic annulus, the balloon catheter having a proximal control handle on which are mounted both a deflection actuator for deflecting the balloon and the heart valve relative to a proximal section of the catheter and a pusher actuator for longitudinally displacing a valve pusher with respect to the balloon, wherein the valve pusher in a distalmost position surrounds a proximal portion of the balloon;
   using one hand on the control handle, moving the deflection actuator to deflect the balloon catheter and the heart valve relative to the aortic annulus and moving the pusher actuator to retract the valve pusher with respect to the balloon; and
   inflating the balloon to expand the heart valve against the aortic annulus.

2. The method of claim 1, wherein the incision is formed at the apex of the left ventricle.

3. The method of claim 1, wherein the introducer is no more than 13 inches (33 cm) long.

4. The method of claim 1, wherein the introducer has a distal section that is more flexible than the stiff proximal section.

5. The method of claim 1, wherein the balloon catheter further comprises a catheter tube and the balloon is disposed on the end of a deflectable portion of the catheter tube actuated by a deflection pull wire which is connected to the deflection actuator.

6. The method of claim 5, wherein the valve pusher slides over the catheter tube and moves longitudinally with respect to the balloon, the valve pusher having a flared distal end that surrounds the proximal portion of the balloon.

7. The method of claim 1, further including a tubular loader defining a throughbore and structure for snapping onto a proximal end of the introducer, the loader having a distal nose that extends through and opens an introducer valve and facilitates passage therethrough of the balloon of the balloon catheter, wherein the method includes single-handedly aspirating air from within the loader throughbore using a vent button on the loader after the heart valve has been inserted into the introducer through the loader.

8. A method of deploying and implanting a prosthetic heart valve into a beating heart, comprising:
   while the heart is beating, forming an incision and passing an introducer into the left side of the heart, the introducer including a proximal hemostatic valve to help prevent blood loss therethrough;
   attaching a tubular loader to a proximal end of the introducer, the loader defining a throughbore and structure for engaging mating structure on the introducer, the loader having a distal nose that extends through and opens the introducer valve;

advancing a balloon catheter having a heart valve mounted on a distal balloon into and through the loader throughbore and into the introducer;

single-handedly aspirating air from within the loader throughbore using a vent button on the loader after the heart valve has been inserted into the introducer through the loader;

further advancing the balloon catheter and positioning the heart valve within the aortic annulus; and inflating the balloon to expand the heart valve against the aortic annulus.

9. The method of claim 8, wherein the incision is formed at the apex of the left ventricle.

10. The method of claim 8, wherein the loader has a proximal housing with a resilient vent member therein, and the vent button project through apertures in the side of the proximal housing and are positioned such that inward depression of the button causes deformation of the vent member which in turn opens the loader throughbore to the atmosphere.

11. The method of claim 8, wherein there are two vent buttons on opposite sides of a proximal housing of the loader.

12. The method of claim 8, wherein the introducer is no more than 13 inches (33 cm) long.

13. The method of claim 8, wherein the introducer has a distal section that is more flexible than a stiff proximal section.

14. The method of claim 8, wherein the balloon catheter further comprises a catheter tube and the balloon is disposed on the end of a deflectable portion of the catheter tube actuated by a deflection pull wire, and the balloon catheter further includes a proximal control handle on which is mounted a deflection actuator for deflecting the deflectable portion of the catheter tube, the method including displacing the deflection actuator to deflect the distal end of the balloon catheter during the step of positioning the heart valve within the aortic annulus.

* * * * *